(12) United States Patent
Nyman et al.

(10) Patent No.: US 12,329,369 B2
(45) Date of Patent: Jun. 17, 2025

(54) TISSUE CLOSURE DEVICE

(71) Applicant: Arterica Inc., Santa Rosa, CA (US)

(72) Inventors: Henrik Nyman, Olofstorp (SE); Robert G. Whirley, Petaluma, CA (US); Cecilia Larzon, Stockholm (SE); Joseph W. Humphrey, Santa Rosa, CA (US)

(73) Assignee: ARTERICA INC., Santa Rosa, CA (US)

( * ) Notice: Subject to any disclaimer, the term of this patent is extended or adjusted under 35 U.S.C. 154(b) by 0 days.

(21) Appl. No.: 18/538,926

(22) Filed: Dec. 13, 2023

(65) Prior Publication Data

US 2024/0108321 A1  Apr. 4, 2024

Related U.S. Application Data

(62) Division of application No. 16/190,694, filed on Nov. 14, 2018, now abandoned.
(Continued)

(51) Int. Cl.
*A61B 17/00* (2006.01)
*A61B 17/04* (2006.01)
(Continued)

(52) U.S. Cl.
CPC ...... *A61B 17/0057* (2013.01); *A61B 17/0401* (2013.01); *A61B 17/12109* (2013.01);
(Continued)

(58) Field of Classification Search
CPC ............ A61B 17/0057; A61B 17/0401; A61B 17/12109; A61B 17/12013; A61B 17/1227; A61B 2017/00349; A61B 2017/00575; A61B 2017/0065; A61B 2017/00663; A61B 2017/00668; A61B 2017/00672; A61B 2017/00676; A61B 2017/00778;
(Continued)

(56) References Cited

U.S. PATENT DOCUMENTS 5,364,408 A   11/1994   Gordon
5,417,699 A   5/1995    Klein et al.
(Continued)

FOREIGN PATENT DOCUMENTS

EP   2095774   9/2009
EP   2308521   4/2011
(Continued)

OTHER PUBLICATIONS

Invitation to Pay Additional Fees dated: Feb. 20, 2024 in International Application No. PCT/US2023/078087 filed: Oct. 27, 2023.
(Continued)

*Primary Examiner* — Kelly J Bekker
*Assistant Examiner* — Andrew P. Restaino
(74) *Attorney, Agent, or Firm* — Schmeiser, Olsen & Watts LLP

(57) ABSTRACT

Device and method embodiments discussed herein are directed to mechanical closure of an access passage in a tissue layer adjacent to an access hole in a vessel such as an artery or vein of a patient. Some of these embodiments may also be applicable to direct closure of a vessel wall in some instances.

16 Claims, 20 Drawing Sheets

Related U.S. Application Data

(60) Provisional application No. 62/587,353, filed on Nov. 16, 2017.

(51) Int. Cl.
*A61B 17/06* (2006.01)
*A61B 17/12* (2006.01)
*A61B 17/122* (2006.01)
*A61B 17/29* (2006.01)

(52) U.S. Cl.
CPC ............... *A61B 2017/00349* (2013.01); *A61B 2017/00575* (2013.01); *A61B 2017/0065* (2013.01); *A61B 2017/00663* (2013.01); *A61B 2017/00668* (2013.01); *A61B 2017/00672* (2013.01); *A61B 2017/00676* (2013.01); *A61B 2017/00778* (2013.01); *A61B 2017/00862* (2013.01); *A61B 2017/00867* (2013.01); *A61B 2017/0409* (2013.01); *A61B 2017/0427* (2013.01); *A61B 2017/0619* (2013.01); *A61B 2017/12004* (2013.01); *A61B 17/12013* (2013.01); *A61B 17/1227* (2013.01); *A61B 2017/2906* (2013.01)

(58) Field of Classification Search
CPC ........... A61B 2017/00862; A61B 2017/00867; A61B 2017/0409; A61B 2017/0427; A61B 2017/0619; A61B 2017/12004; A61B 2017/2906

See application file for complete search history.

(56) References Cited

U.S. PATENT DOCUMENTS

| | | | |
|---|---|---|---|
| 5,507,755 | A | 4/1996 | Gresl et al. |
| 5,540,704 | A | 7/1996 | Gordon et al. |
| 5,700,273 | A | 12/1997 | Buelna et al. |
| 5,716,375 | A | 2/1998 | Fowler |
| 5,807,326 | A | 9/1998 | O'Neill et al. |
| 5,836,913 | A | 11/1998 | Orth et al. |
| 5,860,990 | A | 1/1999 | Nobles et al. |
| 5,868,762 | A | 2/1999 | Cragg et al. |
| 6,048,357 | A | 4/2000 | Kontos |
| 6,059,800 | A | 5/2000 | Hart et al. |
| 6,077,279 | A | 6/2000 | Kontos |
| 6,110,184 | A | 8/2000 | Weadock |
| 6,231,561 | B1 | 5/2001 | Frazier et al. |
| 6,238,412 | B1 | 5/2001 | Dubrul et al. |
| 6,328,758 | B1 | 12/2001 | Tornier et al. |
| 6,461,366 | B1 | 10/2002 | Seguin |
| 6,626,918 | B1 | 9/2003 | Ginn et al. |
| 6,669,719 | B2 | 12/2003 | Wallace et al. |
| 7,458,978 | B1 | 12/2008 | Bender et al. |
| 8,414,528 | B2 | 4/2013 | Liu et al. |
| 8,617,204 | B2 | 12/2013 | Khosravi et al. |
| 8,821,532 | B2 | 9/2014 | Schaeffer |
| 8,920,442 | B2 | 12/2014 | Sibbitt, Jr. et al. |
| 9,017,374 | B2 | 4/2015 | Yassinzadeh |
| 9,782,156 | B2 | 10/2017 | Larzon et al. |
| 2002/0026208 | A1 | 2/2002 | Roe et al. |
| 2002/0045908 | A1* | 4/2002 | Nobles ............... A61B 17/0057 606/144 |
| 2003/0233120 | A1 | 12/2003 | Akerfeldt |
| 2004/0087967 | A1* | 5/2004 | Schur ............... A61B 17/00008 606/108 |
| 2004/0097978 | A1 | 5/2004 | Modesitt et al. |
| 2004/0220522 | A1 | 11/2004 | Brisco et al. |
| 2005/0121042 | A1 | 6/2005 | Belhe et al. |
| 2005/0149066 | A1 | 7/2005 | Stafford |
| 2005/0155608 | A1 | 7/2005 | Pavcnik et al. |
| 2005/0251155 | A1 | 11/2005 | Orban, III |
| 2005/0267528 | A1 | 12/2005 | Ginn et al. |
| 2006/0069397 | A1 | 3/2006 | Nobles et al. |
| 2006/0089627 | A1 | 4/2006 | Burnett et al. |
| 2006/0135991 | A1 | 6/2006 | Kawaura et al. |
| 2006/0142784 | A1 | 6/2006 | Kontos |
| 2007/0049967 | A1* | 3/2007 | Sibbitt, Jr. ............ A61B 17/10 606/213 |
| 2007/0083231 | A1 | 4/2007 | Lee |
| 2007/0112425 | A1 | 5/2007 | Schaller et al. |
| 2007/0203506 | A1 | 8/2007 | Sibbitt, Jr. et al. |
| 2007/0203507 | A1 | 8/2007 | McLaughlin et al. |
| 2007/0213616 | A1 | 9/2007 | Anderson et al. |
| 2007/0276413 | A1 | 11/2007 | Nobels |
| 2008/0082122 | A1 | 4/2008 | Khosravi et al. |
| 2008/0147112 | A1 | 6/2008 | Sheets et al. |
| 2008/0154303 | A1 | 6/2008 | Yassinzadeh |
| 2008/0177288 | A1 | 7/2008 | Carlson |
| 2008/0287988 | A1 | 11/2008 | Smith et al. |
| 2008/0294001 | A1 | 11/2008 | Surti |
| 2008/0300629 | A1 | 12/2008 | Surti |
| 2009/0143808 | A1* | 6/2009 | Houser ............... A61B 17/0057 606/172 |
| 2009/0248056 | A1 | 10/2009 | Gabel et al. |
| 2009/0254110 | A1 | 10/2009 | Bagaoisan et al. |
| 2009/0254119 | A1 | 10/2009 | Sibbitt, Jr. et al. |
| 2009/0264922 | A1 | 10/2009 | Mas |
| 2009/0306685 | A1 | 12/2009 | Fill |
| 2009/0318936 | A1* | 12/2009 | Harris ................ A61B 17/083 606/220 |
| 2010/0179572 | A1 | 7/2010 | Voss et al. |
| 2010/0179590 | A1* | 7/2010 | Fortson ............... A61B 17/0057 606/216 |
| 2010/0217308 | A1 | 8/2010 | Hanson |
| 2010/0217311 | A1 | 8/2010 | Jenson et al. |
| 2010/0217312 | A1 | 8/2010 | Hill et al. |
| 2010/0262166 | A1 | 10/2010 | Boraiah et al. |
| 2011/0077668 | A1* | 3/2011 | Gordon ................ A61B 17/10 606/151 |
| 2011/0218568 | A1 | 9/2011 | Voss |
| 2011/0238090 | A1 | 9/2011 | Heneveld |
| 2011/0301619 | A1 | 12/2011 | Walters |
| 2012/0010633 | A1* | 1/2012 | Noda ............... A61B 17/12013 606/140 |
| 2012/0158045 | A1 | 6/2012 | Pipenhagen |
| 2012/0290001 | A1 | 11/2012 | Uchida et al. |
| 2012/0296373 | A1 | 11/2012 | Roorda et al. |
| 2013/0006297 | A1* | 1/2013 | Drasler ............... A61B 17/0057 606/213 |
| 2013/0123812 | A1 | 5/2013 | Tegels |
| 2013/0123844 | A1 | 5/2013 | White |
| 2013/0190812 | A1 | 7/2013 | Vidlund |
| 2013/0231701 | A1 | 9/2013 | Voss et al. |
| 2014/0039547 | A1 | 2/2014 | White |
| 2014/0076955 | A1 | 3/2014 | Lorenz |
| 2014/0214079 | A1 | 7/2014 | Ewers et al. |
| 2015/0005810 | A1 | 1/2015 | Center et al. |
| 2015/0066055 | A1 | 3/2015 | Sibbitt, Jr. et al. |
| 2015/0105805 | A1 | 4/2015 | Fortson |
| 2015/0142049 | A1 | 5/2015 | Delgado et al. |
| 2015/0265350 | A1 | 9/2015 | Shimizu et al. |
| 2015/0289861 | A1 | 10/2015 | MacPhee et al. |
| 2016/0228107 | A1 | 8/2016 | Madsen et al. |
| 2016/0228109 | A1 | 8/2016 | Jacobs et al. |
| 2016/0242793 | A1 | 8/2016 | Norton et al. |
| 2017/0049426 | A1 | 2/2017 | Gianotti et al. |
| 2017/0086804 | A1 | 3/2017 | Larzon et al. |
| 2017/0086807 | A1 | 3/2017 | Larzon et al. |
| 2017/0203082 | A1 | 7/2017 | Foy et al. |
| 2018/0049731 | A1 | 2/2018 | Hardy et al. |
| 2019/0142402 | A1 | 5/2019 | Larzon et al. |
| 2019/0142403 | A1 | 5/2019 | Nyman et al. |
| 2020/0046343 | A1 | 2/2020 | Kramer |
| 2020/0129164 | A1 | 4/2020 | Larzon et al. |
| 2023/0309979 | A1 | 10/2023 | Agnihotri et al. |
| 2024/0138824 | A1 | 5/2024 | Hauck et al. |

FOREIGN PATENT DOCUMENTS

| | | |
|---|---|---|
| EP | 2656816 | 10/2013 |
| EP | 4169453 A1 | 4/2023 |

(56) References Cited

FOREIGN PATENT DOCUMENTS

| GB | 2365342 | 2/2002 |
|---|---|---|
| JP | 2005-511130 | 4/2005 |
| JP | 2013-226414 | 11/2013 |
| WO | 1996/024291 | 8/1996 |
| WO | WO 97/03613 | 2/1997 |
| WO | WO 10/081103 | 7/2010 |
| WO | WO 14/169215 | 10/2014 |
| WO | WO 17/019525 | 2/2017 |
| WO | WO 18/195274 | 10/2018 |
| WO | WO 19/098921 | 5/2019 |
| WO | WO 19/098922 | 5/2019 |
| WO | WO 19/157022 | 8/2019 |
| WO | WO 20/081864 | 4/2020 |
| WO | WO 20/085983 | 4/2020 |
| WO | WO 21/102044 | 5/2021 |
| WO | WO 23/072972 | 5/2023 |
| WO | WO 24/092233 | 5/2024 |

OTHER PUBLICATIONS

Non-Final Office Action dated: Jan. 31, 2024 in U.S. Appl. No. 16/661,261, filed Oct. 23, 2019 and published as: 2020/0129164 on: Apr. 30, 2020.
Bountouris et al., "Endovascular aneurysm repair with Fascia suture technique: short and mid-term results," Int Angiol, Epub Nov. 10, 2015.
Fisher, "The Fascia Suture Technique: This Late Bloomer Could Become a Winner," J. Endovasc Ther, 2012, 19:397-399.
Freitas et al., "The use of closure devices in peripheral endovascular interventions: The Leipzig real-world report," Journal of The American College of Cardiology, TCT Abstracts/Vascular Access and Intervention—Femoral (includes closure devices) Abstract TCT-842, p. B245, Saturday, Sep. 13, 2014, 5:00 PM-7:00 PM.
Harrison et al., "Fascial Closure Following Percutaneous Endovascular Aneurysm Repair," Eur J Vasc Endovasc Surg (2011) 41, 346-349.
Larzon et al., "Editor's Choice—A Randomized Controlled Trial of the Fascia Suture Technique Compared with a Suture-mediated Closure Device for Femoral Arterial Closure after Endovascular Aortic Repair," Eur J Vasc Endovasc Surg (Feb. 2015) 49, 166-173.
Larzon et al., "Fascia Suturing of Large Access Sites After Endovascular Treatment of Aortic Aneurysms and Dissections," J Endovasc Ther, 2006, 13:152-157.
Lee et al., "Midterm outcomes of femoral arteries after percutaneous endovascular aortic repair using the Preclose technique," J Vasc Surg, 2008: 47:919-923.
Mathisen et al., "Complication Rate of the Fascia Closure Technique in Endovascular Aneurysm Repair," J Endovasc Ther 2012; 19:392-396.
Montan et al., "Short- and Midterm Results of the Fascia Suture Technique for Closure of Femoral Artery Access Sites After Endovascular Aneurysm Repair," J Endovasc Ther, 2011; 18:789-796.
Nelson, "Closure and Arterial Access Conundrums" Presentat+A25ion, Saturday Jun. 7, 2014, Society for Vascular Surgery, 2014 Vascular Annual Meeting, Boston, Jun. 5-7.
Wanhainen, A., "Invited Commentary, Commentary on 'A Randomized Controlled Trial of the Fascia Suture Technique Compared with a Suture-mediated Closure Device for Femoral Arterial Closure After Endovascular Aortic Repair'" Eur J Vasc Endovasc Surg (Feb. 2015) 49, 174-174.
International Search Report and Written Opinion dated: Jan. 31, 2017 in International Application No. PCT/IB2016/001498 filed: Sep. 27, 2016.
Non Final Office Action dated: Dec. 15, 2016 in U.S. Appl. No. 15/291,991, filed Oct. 12, 2016, published as US-2017/0086807 on Mar. 30, 2017.
Notice of Allowance dated: May 12, 2017 in U.S. Appl. No. 15/291,991, filed Oct. 12, 2016, published as US-2017/0086807 on Mar. 30, 2017.
Notice of Allowance dated: Nov. 20, 2018 in U.S. Appl. No. 15/611,665, filed Jun. 1, 2017, published as: 2017-0265848 on Sep. 21, 2017.
Notice of Allowance dated: Sep. 19, 2018 in U.S. Appl. No. 15/611,665, filed Jun. 1, 2017, published as: 2017-0265848 on Sep. 21, 2017.
Final Office Action dated: Jan. 10, 2018 in U.S. Appl. No. 15/611,665, filed Jun. 1, 2017, published as: 2017-0265848 on Sep. 21, 2017.
Non-Final Office Action dated: Aug. 9, 2017 in U.S. Appl. No. 15/611,665, filed Jun. 1, 2017, published as: 2017-0265848 on Sep. 21, 2017.
Non-Final Office Action dated: Aug. 16, 2022 in U.S. Appl. No. 16/836,609, filed Mar. 31, 2020, published as: 2020-0245987 on Aug. 6, 2020.
Notice of Allowance dated: Mar. 24, 2023, in U.S. Appl. No. 16/836,609, filed Mar. 31, 2020, published as: 2020-0245987 on Aug. 6, 2020.
Non-Final Office Action dated: Aug. 30, 2018 in U.S. Appl. No. 15/277,542, filed Sep. 27, 2016 published as 2017-0086804 on Mar. 30, 2017.
Final Office Action dated: Apr. 24, 2019 in U.S. Appl. No. 15/277,542, filed Sep. 27, 2016 published as 2017-0086804 on Mar. 30, 2017.
Final Office Action dated: Oct. 3, 2019 in U.S. Appl. No. 15/277,542, filed Sep. 27, 2016 published as 2017-0086804 on Mar. 30, 2017.
Notice of Allowance dated: Jan. 2, 2020 in U.S. Appl. No. 15/277,542, filed Sep. 27, 2016 published as 2017-0086804 on Mar. 30, 2017.
International Search Report and Written Opinion dated: Feb. 13, 2019 in International Application No. PCT/SE2018/051173 filed: Nov. 14, 2018.
International Search Report and Written Opinion dated: Feb. 12, 2019 in International Application No. PCT/SE2018/051172 filed: Nov. 14, 2018.
Extended European Search Report dated: May 13, 2019 in European Patent Application No. EP16850451.2 based on International Patent Application PCT/IB2016/001498 filed: Sep. 27, 2016 and published as: EP3355803 on Aug. 8, 2018.
International Search Report and Written Opinion dated: Jan. 28, 2020 in International Application No. PCT/SE2018/051041 filed: Oct. 23, 2019.
Invitation to Pay Additional Fees dated: Jan. 25, 2021 in International Application No. PCT/US2020/061117 filed: Nov. 18, 2020.
Non-Final Office Action Dated: Mar. 17, 2021 in U.S. Appl. No. 16/190,654, filed Nov. 14, 2018 and published as: 2019-0142402 on May 16, 2019.
International Preliminary Report on Patentability dated: Jun. 2, 2022 in International Application No. PCT/US2020/061117 filed: Nov. 18, 2020 and published as: WO/2021/102044 on May 27, 2021.
International Search Report and Written Opinion dated: Mar. 26, 2021 in International Application No. PCT/US2020/061117 filed: Nov. 18, 2020.
Non-Final Office Action dated: Feb. 8, 2021 in U.S. Appl. No. 16/190,694, filed Nov. 14, 2018 published as: 2019-0142403 on: May 16, 2019.
Final Office Action dated: Aug. 4, 2021 in U.S. Appl. No. 16/190,694, filed Nov. 14, 2018 and published as: 2019/0142403 on: May 16, 2019.
Non-Final Office Action dated: Nov. 18, 2021 in U.S. Appl. No. 16/190,694, filed Nov. 14, 2018 and published as: 2019/0142403 on: May 16, 2019.
Final Office Action dated: Mar. 1, 2022 in U.S. Appl. No. 16/190,694, filed Nov. 14, 2018 and published as: 2019/0142403 on: May 16, 2019.
Non-Office Action dated: Jul. 13, 2022 in U.S. Appl. No. 16/190,694, filed Nov. 14, 2018 and published as: 2019/0142403 on: May 16, 2019.
Final Office Action dated: Nov. 8, 2022 in U.S. Appl. No. 16/190,694, filed Nov. 14, 2018 and published as: 2019/0142403 on: May 16, 2019.
Non-Final Office Action dated: Sep. 13, 2023 in U.S. Appl. No. 16/190,694, filed Nov. 14, 2018 and published as: 2019/0142403 on: May 16, 2019.

(56) References Cited

OTHER PUBLICATIONS

Notice of Allowance and Corrected Notice of Allowability Dated: Aug. 30, 2021 in U.S. Appl. No. 16/190,654, filed Nov. 14, 2018 and published as: 2019-0142402 on May 16, 2019.

Final Office Action dated: Sep. 13, 2023 in U.S. Appl. No. 16/661,261, filed Oct. 23, 2019 and published as: 2020/0129164 on: Apr. 30, 2020.

Non-Final Office Action dated: Jan. 4, 2023 in U.S. Appl. No. 16/661,261, filed Oct. 23, 2019 and published as: 2020/0129164 on: Apr. 30, 2020.

Final Office Action dated: Sep. 7, 2022 in U.S. Appl. No. 16/661,261, filed Oct. 23, 2019 and published as: 2020/0129164 on: Apr. 30, 2020.

Non-Final Office Action dated: Mar. 15, 2022 in U.S. Appl. No. 16/661,261, filed Oct. 23, 2019 and published as: 2020/0129164 on: Apr. 30, 2020.

Extended European Search Report dated: Jul. 11, 2022 in European Patent Application No. EP19875930.0 filed as: PCT/SE2019/051041 on: Oct. 23, 2019.

Notice of Allowance dated: Nov. 14, 2023 in U.S. Appl. No. 16/951,886, filed Nov. 18, 2020 and published as: 2021/0145421 on May 20, 2021.

International Search Report and Written Opinion dated: Apr. 10, 2024 in International Application No. PCT/US2023/078087 filed: Oct. 27, 2023 and published as: WO/2024/092233 on May 2, 2024.

Extended European Search Report dated May 22, 2024 in European Patent Application No. 20891101.6 filed: Nov. 18, 2020.

Non-Final Office Action Dated: May 22, 2024 in U.S. Appl. No. 17/507,640, filed Oct. 21, 2021 and published as: 2022-0039781 on Feb. 10, 2022.

Notice of Allowance dated: Jun. 12, 2024 in U.S. Appl. No. 16/661,261, filed Oct. 23, 2019 and published as: 2020/0129164 on: Apr. 30, 2020.

* cited by examiner

TISSUE CLOSURE DEVICE

RELATED APPLICATIONS

The present application is a divisional of co-pending U.S. patent application Ser. No. 16/190,694, filed Nov. 14, 2018, by Henrik NYMAN et al. titled "TISSUE CLOSURE DEVICE", which claims priority from U.S. Provisional Patent Application Ser. No. 62/587,353, filed Nov. 16, 2017, by Henrik NYMAN et al. titled "Device for Mechanical Approximation of Fascia", each of which is incorporated by reference herein in its entirety.

BACKGROUND

In many percutaneous cardiovascular procedures, a catheter is inserted into an artery, such as the femoral artery, through a percutaneous vascular access. The catheter may be inserted, typically over a guidewire, directly into an artery (a "bareback" procedure), or the catheter may be inserted through a vascular introducer. When the procedure is complete, the physician removes the catheter and then removes the introducer from the vessel (if one was used). The physician then must prevent or limit the amount of blood that leaks through the vascular access. Physicians currently use a number of methods to close the vascular access, such as localized external compression, suture-mediated closure devices, plugs, gels, foams and similar materials.

However, such closure procedures may be time consuming, and may consume a significant portion of the time of the procedure. In addition, existing methods are associated with complications such as hematoma or thromboses. Still further, some of such procedures, particularly suture-mediated closure devices, are known to have high failure rates in the presence of common vascular disease such as atherosclerosis and calcification.

SUMMARY

Some embodiments of a vascular closure device may include a housing having an elongate configuration with an axial length greater than a transverse dimension thereof. Such a housing may further include a proximal end, a distal end and a distal section. A plurality of anchor deployers are slidably disposed within the housing adjacent each other at the distal section of the housing and are configured to extend and spread from the distal section of the housing. Each of the anchor deployers may include a deployment rod which is slidably disposed relative to the housing and which includes an elongate resilient configuration. Each deployment rod may also include a distal end that extends distally and radially from the distal section of the housing so as to spread out from other deployment rod distal ends. In some cases, the deployment rods may be configured to extend distally at the same time or simultaneously. Each anchor deployer may also include an anchor which is secured to the distal end of the deployment rod and which is configured to grip tissue such as the tissue of a fascia tissue layer. The vascular closure device embodiment may further include a tissue grip which is deployable from the distal end of the housing.

Some embodiments of a method for vascular closure may include disposing a distal end of the housing of the vascular closure device to a position adjacent the passage in the tissue layer and deploying a plurality of anchor deployers from a distal section of the housing. The anchor deployers may be so deployed by distally advancing deployment rods of the anchor deployers in a distal and radially outward direction from the housing into the tissue layer in positions disposed about the passage in the tissue layer. Respective anchors of the anchor deployers may then be secured to the tissue layer in positions disposed about the passage in the tissue layer. The deployment rods may then be proximally retracted back into the distal section of the housing so as to draw the anchors and respective tissue layer portions secured thereto together adjacent the distal section of the housing to gather the tissue and close the passage in the tissue layer. Thereafter, a tissue grip may be deployed over the anchors and onto the tissue layer portions gathered and secured to the anchors so as to secure the tissue layer portions together with the access hole closed or reduced. The anchors may then be released from the tissue layer portions which are secured together.

Some embodiments of a method for vascular closure may include disposing a distal end of the housing of the vascular closure device to a position adjacent the passage in the tissue layer and deploying a plurality of anchor deployers from a distal section of the housing. The anchor deployers may be so deployed by distally advancing deployment rods of the anchor deployers in a distal and radially outward direction from the housing into the tissue layer in positions disposed about the passage in the tissue layer. Respective anchors of the anchor deployers may then be secured to the tissue layer in positions disposed about the passage in the tissue layer. The deployment rods may then be proximally retracted back into the distal section of the housing so as to draw the anchors and respective tissue layer portions secured thereto together adjacent the distal section of the housing to gather the tissue and close the passage in the tissue layer. Thereafter, a tissue grip may be deployed over the anchors and onto the tissue layer portions gathered and secured to the anchors so as to secure the tissue layer portions together with the access hole closed or reduced. The anchors may then be detached from each of the respective deployment rods secured thereto and left in the patient secured to the tissue layer.

Some embodiments of a method for vascular closure may include disposing a vascular closure device adjacent a passage in a tissue layer which is disposed above and adjacent an access hole in a blood vessel of a patient and deploying a plurality of anchors from a distal section of the vascular closure device in a distal and radially outward direction therefrom. The method may also include engaging the tissue layer in positions disposed about the passage in the tissue layer with the anchors and securing the anchors to the tissue layer in the positions disposed about the passage in the tissue layer. Thereafter, the anchors may be proximally retracted closer together so as to draw the anchors and respective tissue layer portions secured thereto together thereby closing the passage in the tissue layer. A tissue grip may then be deployed onto the tissue layer portions drawn together by the anchors so as to secure the drawn together tissue layer portions thereby closing the passage in the tissue layer and achieving vascular closure of the access hole in the blood vessel.

Certain embodiments are described further in the following description, examples, claims and drawings. These features of embodiments will become more apparent from the following detailed description when taken in conjunction with the accompanying exemplary drawings.

The drawings are intended to illustrate certain exemplary embodiments and are not limiting. For clarity and ease of illustration, the drawings may not be made to scale, and in some instances, various aspects may be shown exaggerated or enlarged to facilitate an understanding of particular embodiments.

DETAILED DESCRIPTION

After a minimally invasive vascular procedure, a hole in the form of an access passage or the like may be left in a major vessel at an access site that must be closed. Methods for percutaneous closure of such a hole may include remote suturing of the vessel, plugging the hole, and remote suturing of the fascia adjacent to the vessel. Certain device and method embodiments discussed herein are directed to mechanical closure of an access passage in the fascia tissue layer adjacent to an access hole in a vessel such as an artery or vein of a patient. Some of these embodiments may also be applicable to direct closure of an arterial wall in some instances. Some vascular closure device and method embodiments discussed herein may provide a robust and easy-to-use device for closing a vascular access hole after a minimally invasive procedure. In some cases, vascular closure device embodiments discussed herein may be useful for closing large vascular access holes. In addition, certain vascular closure device and method embodiments are discussed in U.S. patent application Ser. No. 15/277,542, filed Sep. 27, 2016, by Thomas Larzon, et al., entitled VASCULAR CLOSURE DEVICE, which is incorporated by reference in its entirety.

Figure 1:
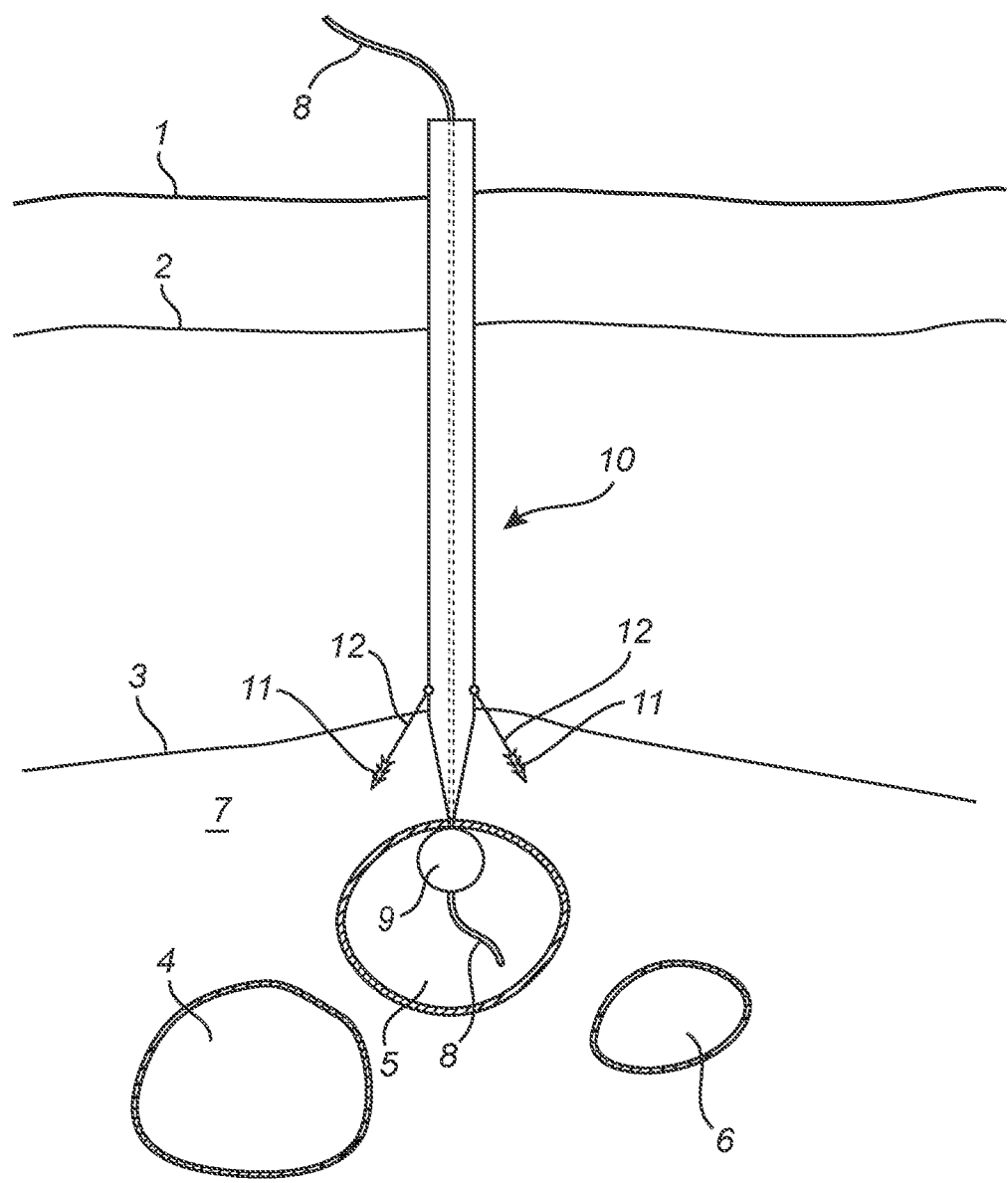
FIG. 1 schematically exemplifies a first embodiment of a vascular closure device according to a possible embodiment of the present disclosure.

The following discussion of the device and method embodiments of FIGS. 1-4B is directed generally to closure of a vascular access passage as well as axial positioning of certain portions of vascular closure device embodiments during such a closure procedure. Such axial positioning devices and methods may be applied to and used with any appropriate vascular closure device or method of embodiment discussed herein. Turning now to the drawings, and to FIG. 1 in particular, an embodiment of a vascular closure device 10 is introduced percutaneously over a guide wire 8 into a blood vessel/artery 5, through the skin 1 and the fascia lata 2 of a patient. An optional anvil member 9 may be arranged inside the blood vessel 5 to create a reference point along an axial orientation to the engagement members 11 and/or for controlling bleeding from an inner lumen of the artery 5. The engagement members 11 may then be placed and released through the vascular closure device 10 and may attach to fascia tissue 3 proximate to the blood vessel 5 and may involve the fascia membrane 3 (fascia iliacus), but, in some instances, not a wall 22 of the blood vessel 5. The engagement members 11 may for example be pushed out of the vascular closure device 10 and into the fascia membrane 3 using deployment members provided as pusher rods 12 arranged in independent lumens provided with the vascular closure device 10, for example through a pusher assembly in a common lumen that simultaneously deploys all engagement members 11, through a spring-loaded mechanism or the like. For some embodiments, the engagement members 11 may be connected with a single filament such as a suture or a plurality of filaments or sutures 13. In FIG. 1 there is further shown a femoral vein 4, a femoral nerve 6 and adjacent/interstitial tissues 7.

Figure 2A:
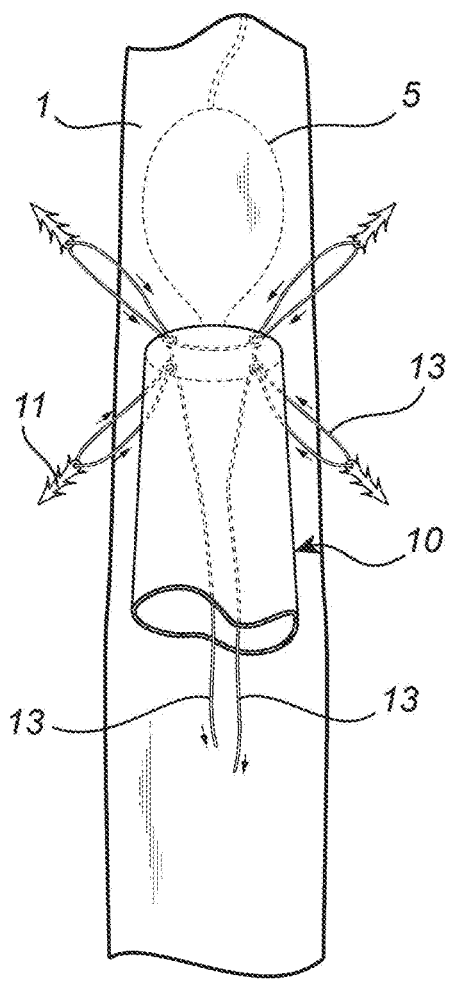
FIGS. 2A and 2B show a detailed view of the creation of a tissue lock using the vascular closure device.
Figure 2B:
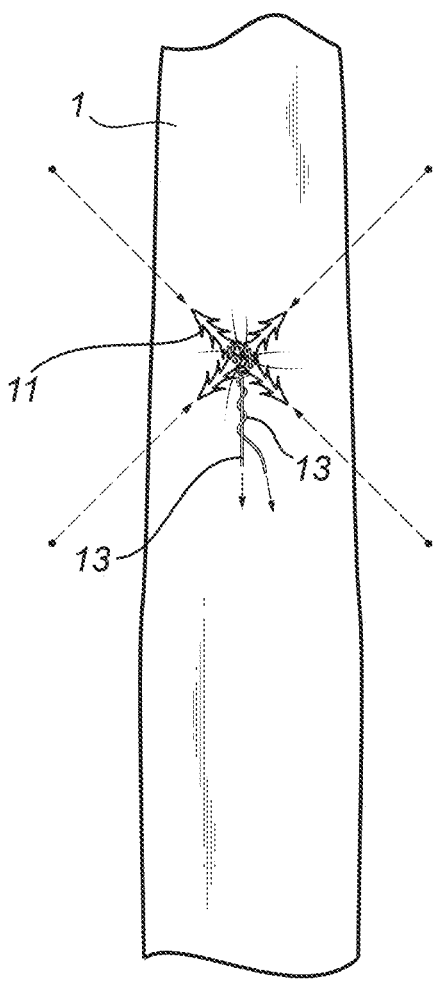

With further reference to FIGS. 2A and 2B, the suture 13 may for example be routed through each of the engagement members 11 in sequence. In particular, one suture 13 may be looped through each of the engagement members 11 in sequence, or a separate suture 13 may be attached to each engagement member 11. The tissue, e.g. fascia membrane 3, may then pulled together in a radially inward direction towards an access passage in the fascia layer 3 with the suture 13 connected to the engagement members 11. When pulled together, the tissue/fascia membrane 3 is tightened towards the center and the access passage therethrough and may then create a tissue lock, thereby indirectly sealing the access hole 16 in the artery 5. That is, a distance between the initial position of the engagement members 11 and a distance between the engagement members once the engagement members 11 have been moved radially inward towards each other is thereby reduced. When tightening the fascia membrane 3 the anvil member 9 may be removed from the artery 5.

Figure 2C:
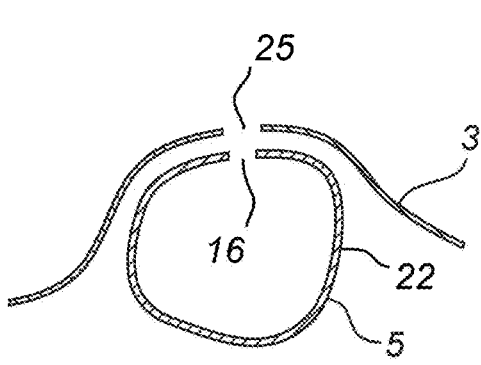
FIGS. 2C and 2D illustrate a closure sequence for treatment of an unwanted passage through a wall of a blood vessel without directly engaging the blood vessel.
Figure 2D:
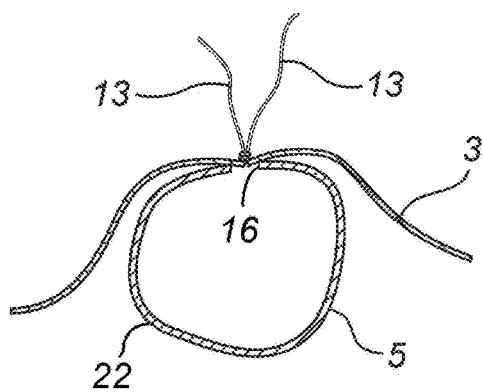

Referring to FIGS. 2C and 2D, an embodiment of a vascular closure sequence is shown whereby a passage 16 through a wall 22 of the vessel 5 such as the blood vessel shown is treated such that leakage of blood from the interior volume of the blood vessel (not shown) is slowed or stopped to a clinically acceptable degree. As seen in FIG. 2C, the passage 16 in the wall of the blood vessel, specifically, the femoral artery 5, is disposed in general alignment with a passage 25 through the fascia tissue layer 3 disposed proximate to an outer surface of the femoral artery 5. For this particular exemplary embodiment, the tissue layer disposed outside of and proximate to the outer surface of the femoral artery 5 is the fascia iliacus 3. For purposes of this general discussion, the phrase "in general alignment" as applied to the respective passages 16, 25 may mean at least that an appropriately sized elongate device such as a catheter or sheath may pass through both passages 16, 25 without significant relative lateral displacement between the tissue 3 and artery 5.

In addition, in some cases, the tissue layer 3 may be disposed sufficiently proximate the outside surface of the blood vessel 5 such that gathering and approximation of the fascia tissue 3 which is disposed about the passage 25 through the tissue 3 so as to close the passage 25 through the tissue/fascia membrane 3 and form a tissue lock is sufficient to tighten and displace the closed gathered tissue/fascia membrane 3 against the outer surface of the artery 5 which is adjacent the passage 16 through the artery 5 as shown in FIG. 2D.

When the gathered tissue 3 has been displaced and deflected so as to be disposed against the passage 16 of the artery 5 and wall of the artery 5 disposed about the passage 16 in the artery 5, this mechanical approximation will typically be sufficient in order to achieve a clinically sufficient slowing or stoppage of blood leakage from the passage 16 in the artery 5 in order to permit closure of an access site through the patient's skin 1 adjacent the passages. In some instances, an inner surface of the tissue layer 3 disposed proximate to the outer surface of the blood vessel 5 may be separated from the outer surface of the blood vessel in the region of the respective passages therethrough by a distance of up to about 10 mm, more specifically, up to about 5 mm.

Figure 3A:
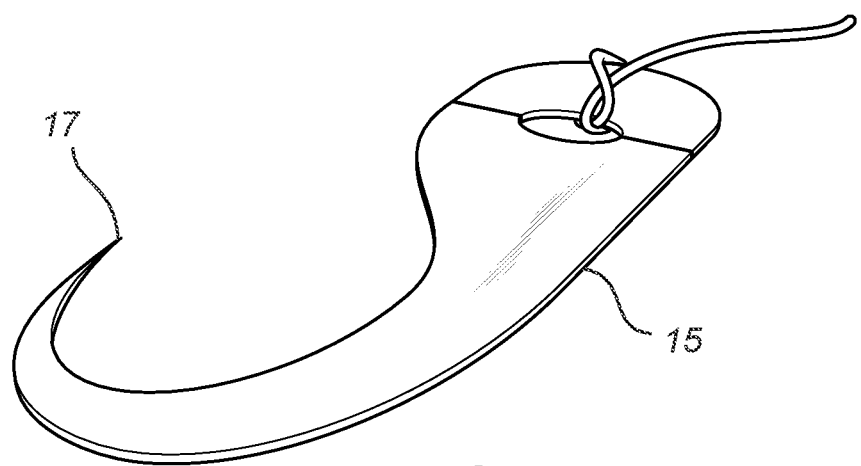
FIGS. 3A and 3B conceptually illustrate an engagement member, exemplified as an anchor element.
Figure 3B:
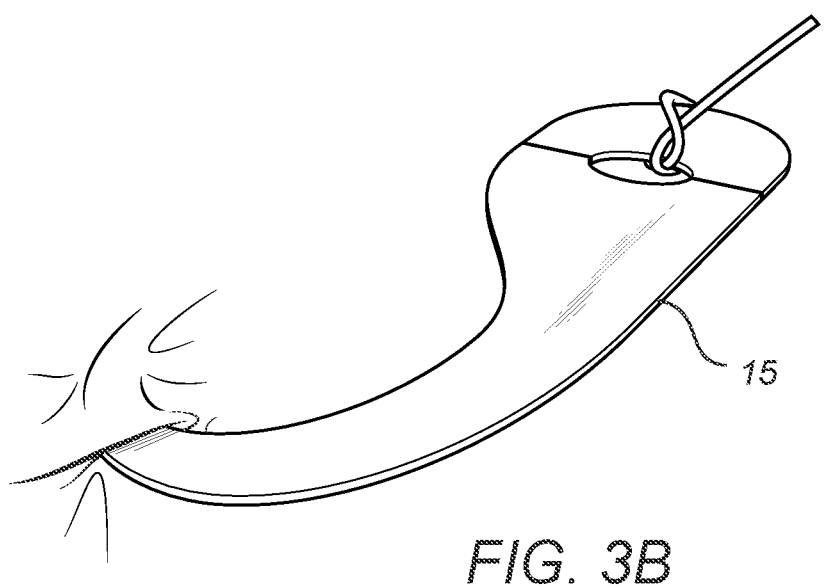

With further reference to FIGS. 3A and 3B, there is conceptually illustrated an engagement member, exemplified as an anchor element 15. In FIG. 3A, the anchor element 15 is shown as initially deployed, so that it slides easily in the direction away from a deployment point. Note that the deployment point may optionally be deflected toward the tissue/fascia membrane 3 to promote engagement. FIG. 3B shows the anchor element 15 after motion has been reversed toward the deployment point, and the anchor element 15 has embedded into the tissue/fascia membrane 3. That is, a tip 17 of the anchors element 15 is in one embodiment hook-shaped, so that it easily slides outward without engaging the tissue/fascia membrane 3. However, once the anchor element 15 is retracted, at least the tip 17 of the anchor element 15 is adapted to mechanically engage with the tissue/fascia membrane 3.

Figure 4A:
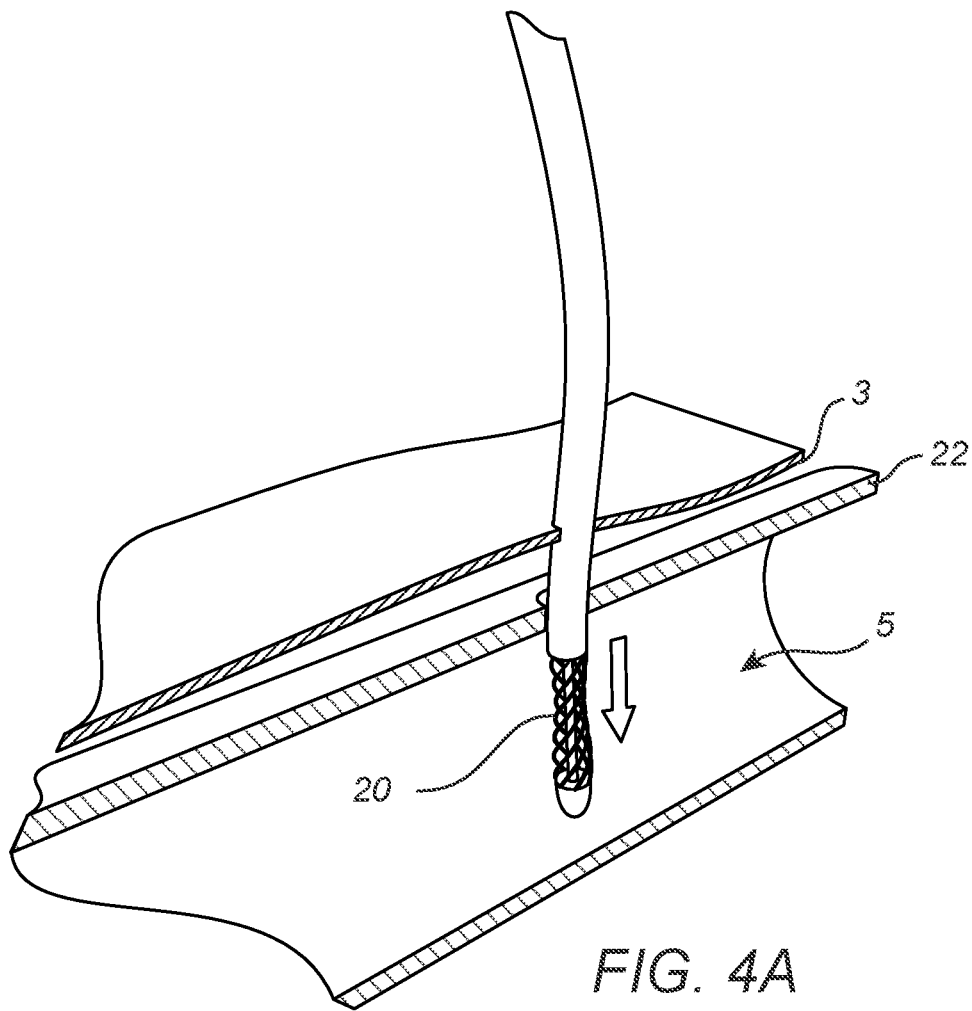
FIGS. 4A and 4B illustrate the operation of an anvil member that functions as a deployable positioning feature.
Figure 4B:
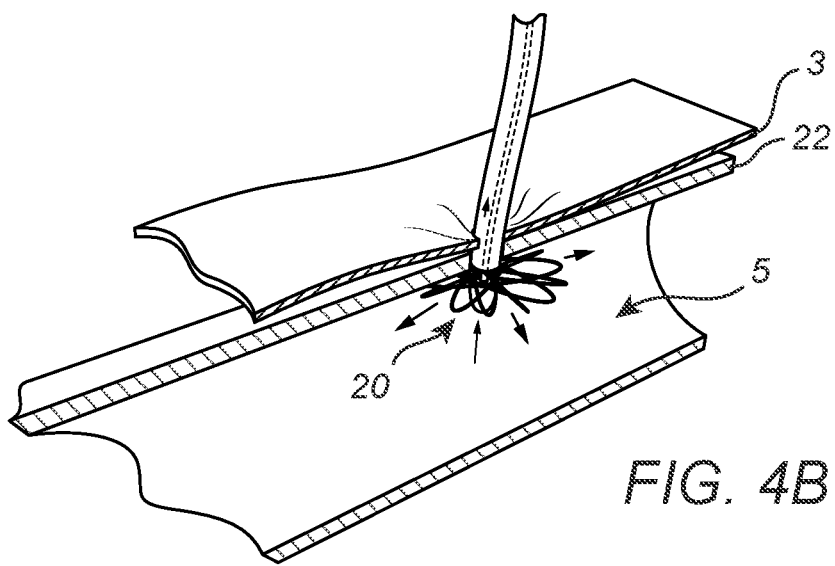

FIGS. 4A and 4B conceptually illustrate the operation of an anvil member exemplified as a deployable positioning feature 20. In FIG. 4A, deployable positioning feature 20 may be inserted through the wall 22 and into the interior volume of the blood vessel, such as the femoral artery 5. The deployable positioning feature 20 may be structured similar to an umbrella (using a mesh material), where the deployable positioning feature 20 in a radially collapsed form may be inserted into the artery 5. Once within the artery 5, with further reference to FIG. 4B, the deployable positioning feature 20 may be "unfolded" and radially expanded from the collapsed form such that a total surface area proximate to the longitudinal axis of the deployable positioning feature 20 is increased and thus may be retracted towards the interior wall of the artery 5. Accordingly, a reference point may be thereby established for further operation of the vascular closure device 10.

For the vascular closure device embodiments 24 shown in FIGS. 5-24, a mechanical "grabber" type device may be used to grab the fascia tissue layer 3 around an access hole 25 in the fascia (see FIG. 15), pull it together, and apply a tissue grip type of device such as lock ring 27 or other tissue grip type retention mechanism such as a tissue adhesive 30 directly to the tissue of the fascia 3 to secure the gathered fascia tissue 32 disposed around the access hole 25 in the closed position to form a tissue lock and achieve vascular closure of an access hole 16 in the adjacent vessel 5. FIGS. 5-24 illustrate embodiments of such grabber-type vascular closure devices 24. The arms, also referred to herein as anchor deployers 26, may be initially retracted into a housing 28 to achieve a low profile. Once placed above the fascia tissue layer 3, the arms 26 may be extended distally and radially outward. Due to their preformed curved shape formed from an elastic resilient material (such as stainless steel or nitinol), the arms 26 may be configured to spread out into a radially dispersed pattern disposed around the access hole 25 in the fascia tissue layer 3.

The arms 26 may then engage the fascia tissue layer 3 at two or more points around the access hole 25. This engagement may be accomplished by an anchor 31 such as a small jaw 34 or the like mounted on the distal end 36 of a deployment rod 38 of each arm 26 and adapted to grab the fascia 3, or a small hook 15, 40 (see FIGS. 3A and 12) could be used to engage the fascia 3. Other similar mechanisms may also be used. Once each arm 26 of the vascular closure device 24 has secured the fascia 3, the housing 28 may be advanced down over the arms 26, or the arms retracted proximally into the housing 28, thereby pulling the distal ends 36 of the arms 26 together in a radially inward and proximal direction, approximating the edges of the fascia tissue layer 3 disposed about the access hole 25 therein, and closing or minimizing the access hole 25.

In addition, the retention mechanism, such as a tissue grip mechanism that holds the approximated edges of the gathered fascia tissue 32 in this gathered configuration, such as the ring or clip 27, may then be deployed onto the gathered tissue 32. Thereafter, the arms 26 or anchors 31 disposed thereon may be disengaged from the fascia tissue layer 3 and the vascular closure device 24 withdrawn from the patient. Suitable tissue retention may be accomplished in some cases by use of the elastic resilient coil in the form of a lock ring 27 that is stretched onto the outside of the housing 28 about an outside circumference of the arms 26 or outside of a translation track of the arms 26. The lock ring 27, which may include an elastic and resilient self-contracting lock ring 27, may be pushed off of the housing 28 by a distal end 42 of a larger, concentric outer tube 44 that lies more proximal over an inner tube 46 of the housing 28. In some cases, the outer tube 44 may be actuated to advance distally relative to the inside tube 46 and deploy the lock ring 27 by advancing a lock ring actuator lever 47 which may be operatively coupled to the outer tube 44. Once pushed off the inside tube 46 of the housing 28 and onto the gathered tissue 32, such an elastic coil 27 may self-contract to circumferentially compress the gathered tissue 32 and brought together by the arms 26 in an inner radial direction and retain the gathered tissue 32 in a bunched or gathered configuration, thereby closing or reducing the access hole 25.

Such elastic coil embodiments 27 may be made from high strength resilient materials such as stainless steel, nitinol, or the like. Some elastic coil embodiments 27 may also be made from or include bioresorbable and/or biodegradable materials. In some embodiments, the gathered tissue 32 may be held together by a biocompatible, rapidly curing tissue adhesive, such as cyanoacrylate, dispensed from a distal section 48 of the housing 28. Such a tissue adhesive 30 may be dispensed as the gathered tissue of the fascia tissue layer 3 is coming together, to facilitate the apposition of surfaces containing tissue adhesive 30, or the tissue adhesive 30 may be dispensed onto the gathered tissue 32 once the tissue is bunched together.

Figure 5:
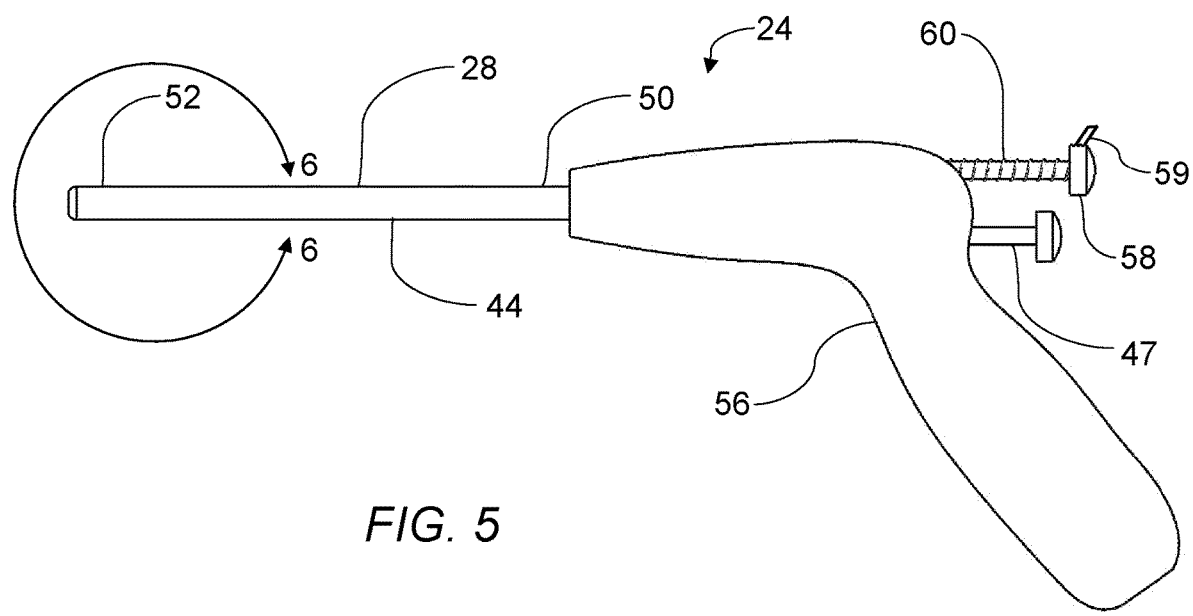
FIG. 5 is an elevation view of a vascular closure device embodiment.
Figure 6A:
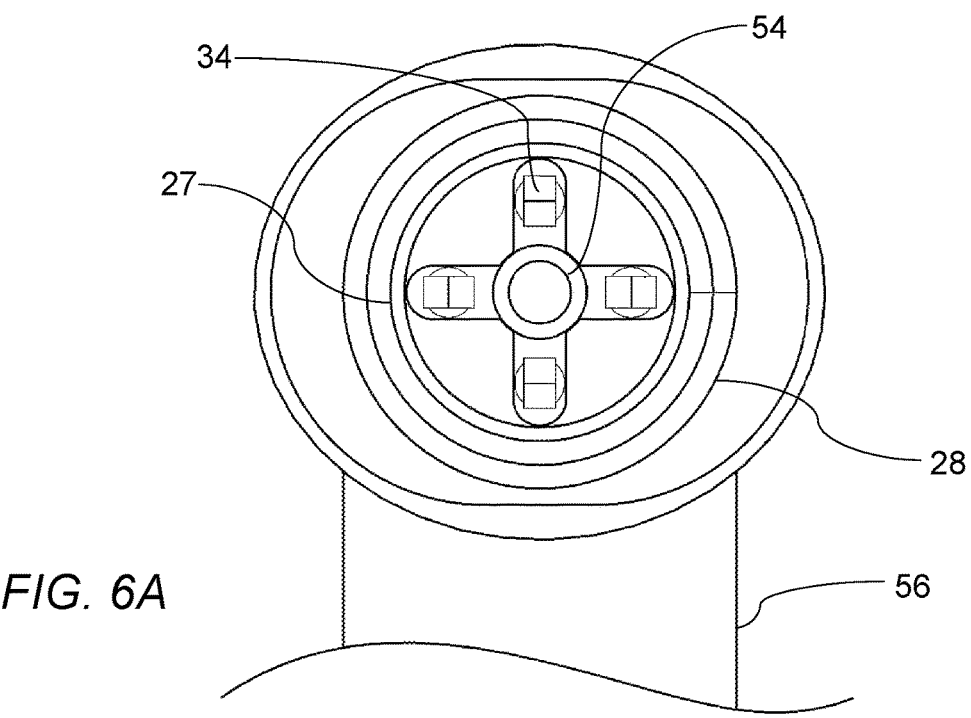
FIG. 6A is a front view of the vascular closure device embodiment of FIG. 5.
Figure 6:
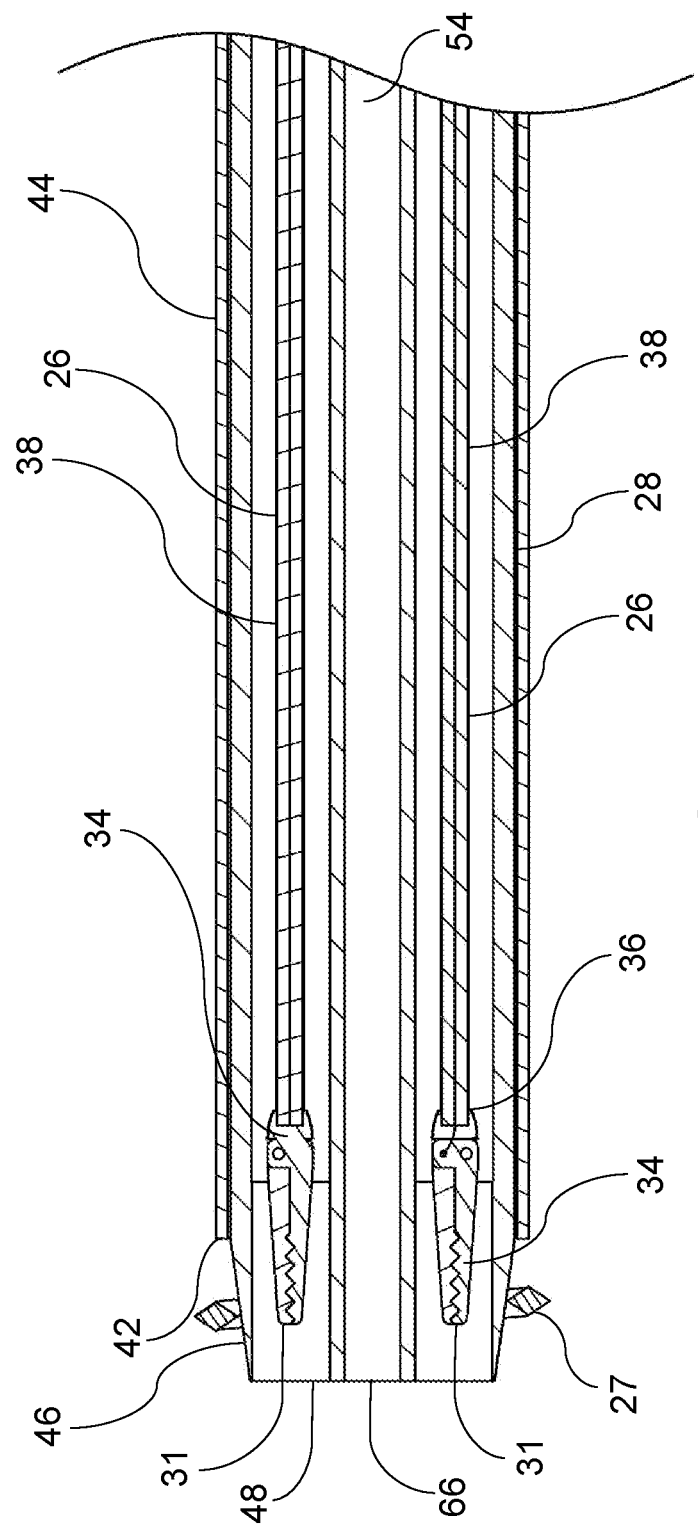
FIG. 6 is an enlarged view of the encircled portion 6-6 of the vascular closure device embodiment of FIG. 5.

Referring to FIGS. 5 and 6, some embodiments of the vascular closure device 24 may include the housing 28 having an elongate configuration with an axial length greater than a transverse dimension thereof. Such a housing 28 may further include a proximal end 50, a distal end 52 and a distal section 48. A plurality of anchor deployers 26 are slidably disposed within the housing 28 adjacent each other at the distal section 48 of the housing 28 and are configured to extend and spread from the distal section 48 of the housing 28. Each of the anchor deployers 26 may include the deployment rod 38 which is slidably disposed relative to the housing 28 and which includes an elongate resilient configuration. Each deployment rod 38 may also include the distal end 36 that extends distally and radially outward from the distal section 48 of the housing 28 so as to spread out from other the distal ends 36 of the deployment rods 38. In some cases, the deployment rods 38 may be configured to extend distally at the same time or simultaneously. Each anchor deployer 26 may also include the anchor 31 which is secured to the distal end 36 of the deployment rod 38 and which is configured to grip tissue such as the tissue of a fascia tissue layer 3. The vascular closure device embodiment 24 may further include the lock ring 27 which may be deployable from the distal end 52 of the housing 28. The vascular closure device of FIG. 5 includes 4 anchor deployers 26, however any suitable number of anchor deployers 26 may be used. Some such vascular closure device embodiments 24 may include about 2 anchor deployers 26 to about 8 anchor deployers 26, more specifically, about 3 anchor deployers 26 to about 5 anchor deployers 26. For some embodiments, it may be desirable for the deployment rods 38 to have a rectangular transverse cross section profile to facilitate distal and radially outward extension while maintaining lateral stability. In some instances, the deployment rod embodiments 38 may have a generally flattened cross section profile with a radial transverse dimension that is less than a circumferentially oriented transverse dimension.

In some cases, the housing 28 may further include a guidewire lumen 54 extending an axial length thereof and a handle 56 secured to the proximal end 50 of the housing 28. A deployment rod pusher 58 which may optionally be spring loaded with a resilient member such as a spring 60 in either a distally biased or proximally biased direction may be operatively coupled to the deployment rods 38 for actuation thereof. For deployment rod pusher embodiments 58 which are proximally biased this may correspond to a bias with the deployment rods 38 biased towards a retracted position which may be overcome by manual pressure in a distal direction against the deployment rod pusher 58. The spring, such as spring 60 shown in FIG. 1, may be used to provide such a resilient biasing force on the deployment rod pusher 58. As shown, the deployment rod pusher 58 is operatively coupled to respective proximal ends of the deployment rods 38 and optionally configured to extend the deployment rods 38 simultaneously in a distal direction upon actuation.

Figure 7A:
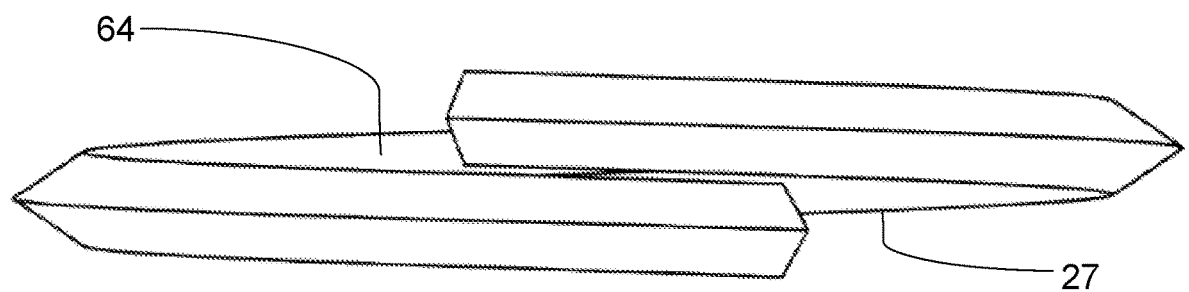
FIG. 7A is an elevation view of a lock ring embodiment.
Figure 7B:
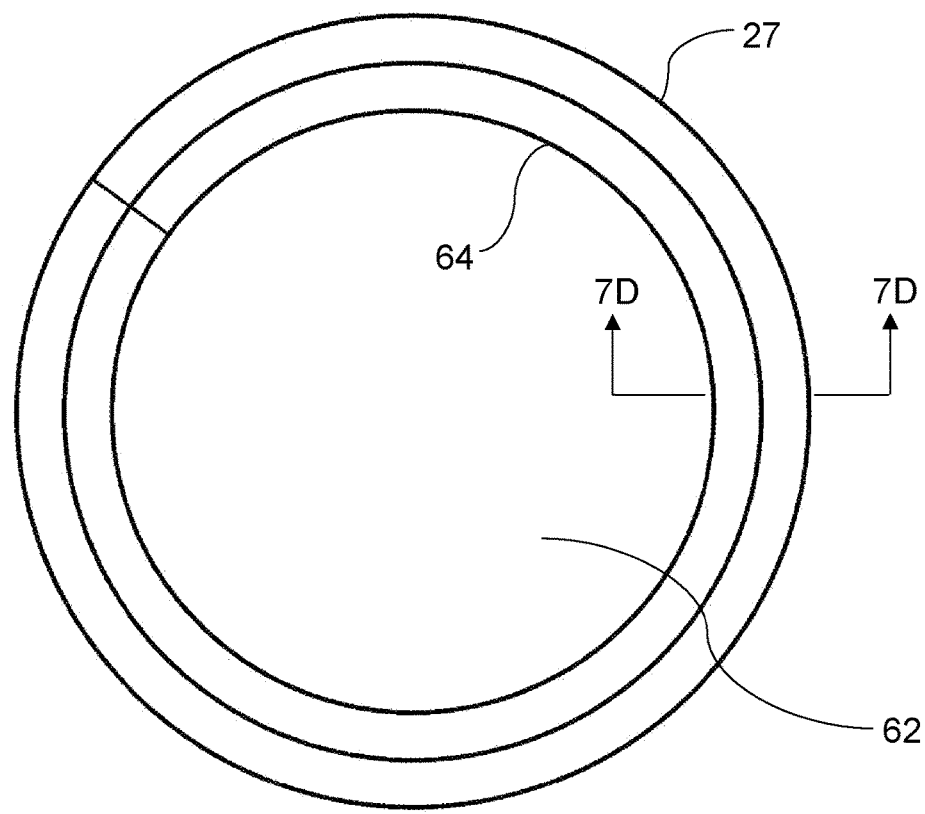
FIG. 7B is a top view of the lock ring embodiment of FIG. 7A.
Figure 7C:
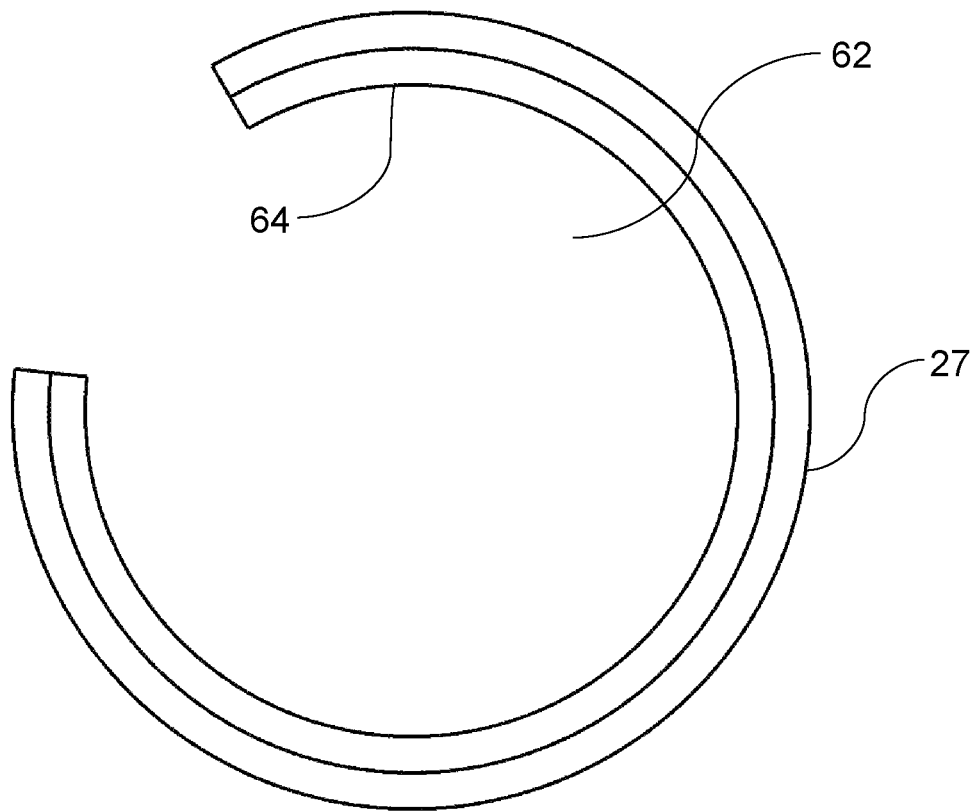
FIG. 7C shows a top view of the lock ring embodiment of FIG. 7A in a radially expanded state.
Figure 7D:
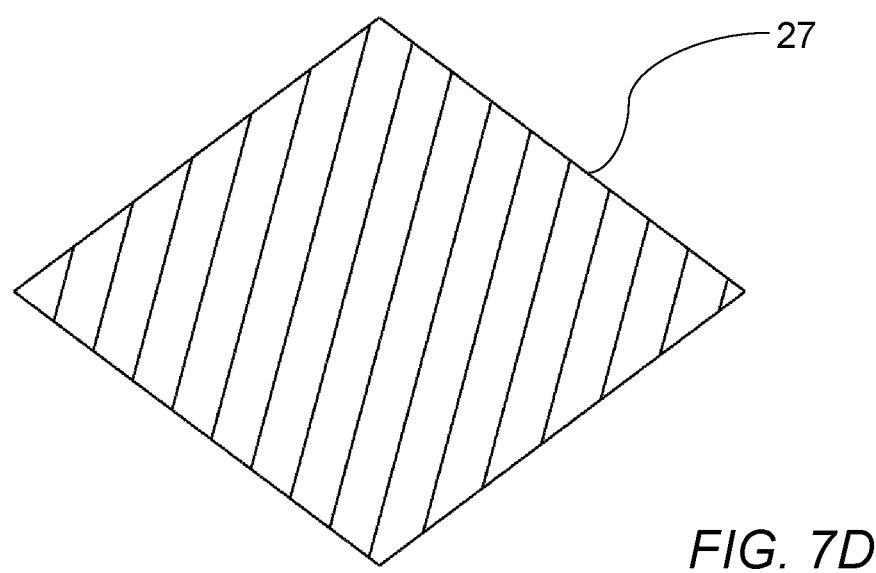
FIG. 7D is a transverse cross section of the lock ring embodiment of FIG. 7B taken along lines 7D-7D of FIG. 7B.
Figure 20:
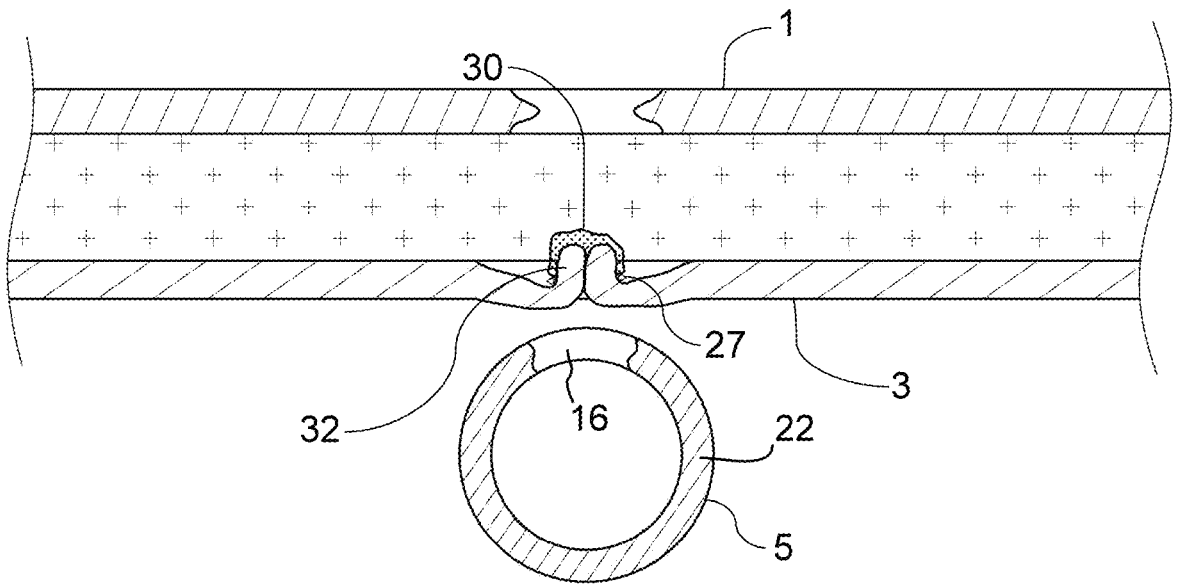
FIG. 20 shows portions of the fascia tissue layer disposed about the access hole in a gathered and secured state with the lock ring and tissue adhesive disposed thereon.
Figure 21:
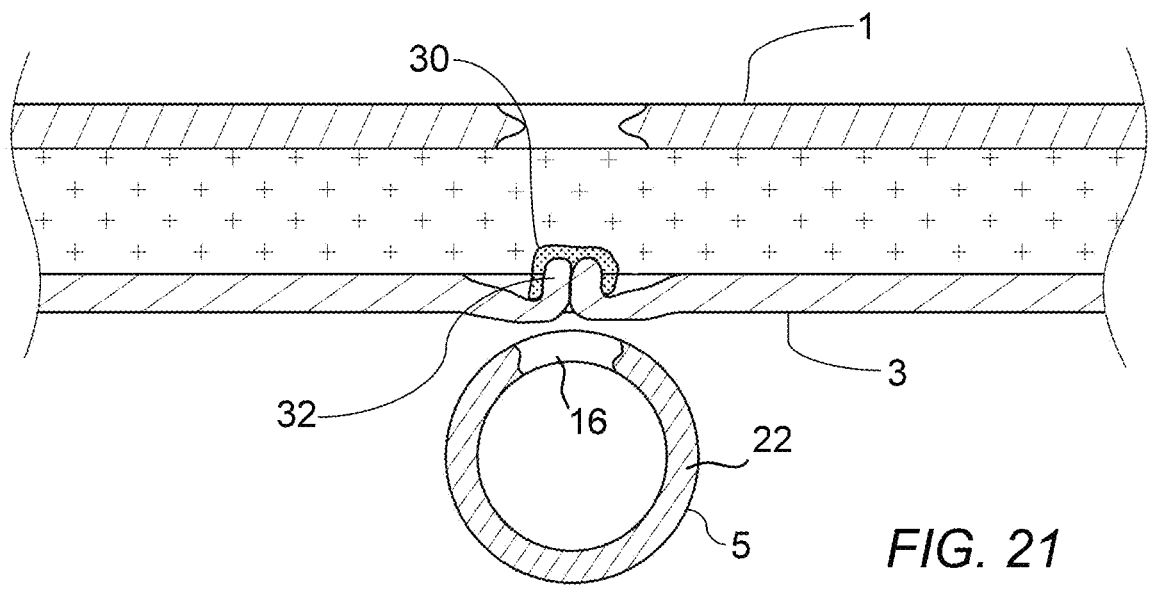
FIG. 21 shows portions of the fascia tissue layer disposed about the access hole in a gathered and secured state with tissue adhesive only disposed thereon.

In some instances, embodiments of a tissue grip mechanism may be disposed on the distal end 52 of the housing 28 around the anchor deployers 26 but generally not in contact with the anchor deployers 26 when in an undeployed state. The tissue grip mechanism may be configured to compress and secure gathered tissue portions 32 relative to each other in some cases. For such embodiments, once the tissue grip is deployed from the distal end 52 of the housing 28 over the anchor deployers 26 and respective anchors 31 thereof and onto the tissue which has been gathered and bunched by the proximally retracted anchor deployers 26, different portions of the gathered tissue are secured in a fixed position relative to each other to form a tissue lock and, in some instances, vascular closure. In some cases, the tissue grip mechanism may include the lock ring 27 disposed about the anchor deployers 26 in the form of a self-retracting coil 27 with a central lumen 62 which may be sized to allow movement of the gathered tissue portions 32 disposed therein while the self-retracting coil 27 is in an expanded state as shown in FIG. 7C. The interior surface 64 of the central lumen 62 may be configured to compress and secure the gathered tissue portions 32 relative to each other when in a retracted compressed state as shown in FIGS. 7A, 7B, 20, and 22. In some cases, embodiments of the tissue grip may include the tissue adhesive 30 that may be dispensed from an outlet port, such as a distal port 66 of the guidewire lumen 54, in the distal end 52 of the housing 28 as shown in FIGS. 20 and 21. For some embodiments, such as the tissue adhesive 30 may include cyanoacrylate, fibrin glue, PEG-based polymers or the like.

Figure 24:
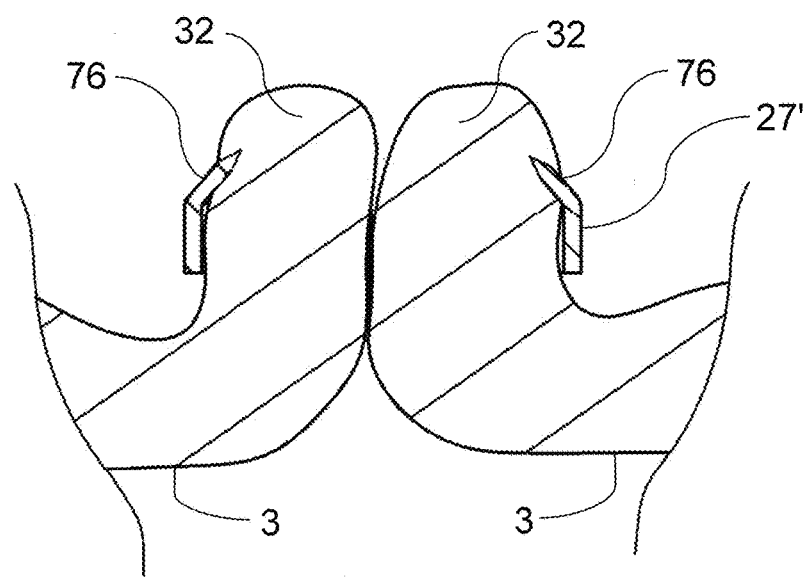
FIG. 24 shows upward and inward facing barb embodiments of the lock ring embodiment of FIG. 23 penetrating into gathered tissue of the portions of fascia tissue layer and mechanically preventing upward movement of the lock ring relative to the fascia tissue.

In general, the tissue grip embodiments such as lock ring 27 and tissue adhesive 30 may optionally include a tissue engagement feature that is configured to stick to a surface of the gathered tissue 32 such as with the tissue adhesive 30 forming a bond with the gathered tissue 32 or sharp inner edge 64 of the diamond profiled lock ring 27 mechanically impinging the gathered tissue 32 so as to effectively secure the tissue portions together. Such tissue engagement features may further include features which may be mechanically captured within the gathered tissue 32 such as the barbs 76 of the "castle shaped" lock ring 27' shown in FIG. 8A. The barbs 76 are configured to penetrate the gathered tissue 32 and be mechanically captured thereby as shown in FIG. 24. All of these tissue engagement feature embodiments may generally be used to keep the tissue grip embodiments from slipping off of the gathered tissue 32 once deployed.

For some embodiments of vascular closure devices 24 discussed herein, the anchors 31 may include releasable anchors. For example, some releasable anchor embodiments may include the jaw 34 that can be moved between an open state and a closed state, each jaw 34 further including an opposed pair of tissue gripping teeth 68 as shown in the anchor embodiment 31 of FIGS. 9-10A and 16A. Such anchors 31 that include a jaw 34, may be actuated by a pull wire 69 or the like that may apply tension to a hinged lever 71 at a proximal end of a hinged jaw portion 73 of the jaw 34 as shown in FIG. 10. In some instances, the pull wire 69 or any other suitable actuation mechanism may be actuated by an actuation lever 59 which may optionally be disposed on the deployment rod pusher 58 shown in FIG. 5.

Figure 11:
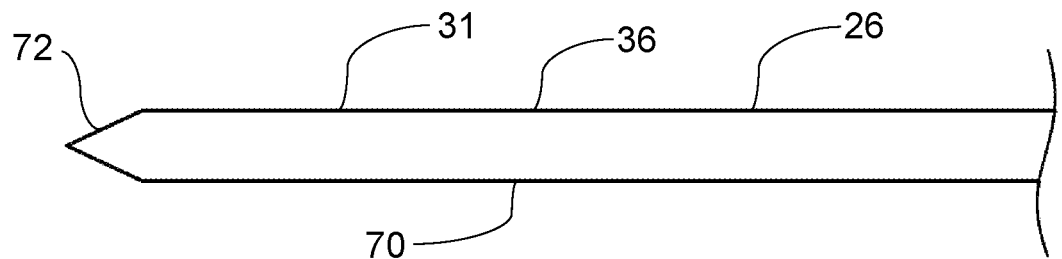
FIG. 11 is an elevation view of a releasable anchor embodiment in a straightened state.
Figure 12:
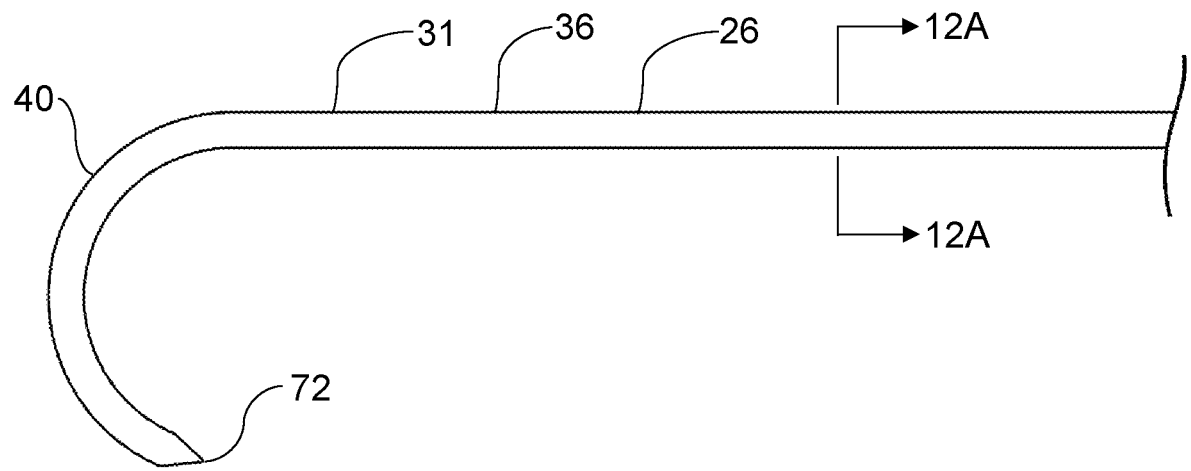
FIG. 12 is an elevation view of the releasable anchor embodiment of FIG. 11 in a curved, tissue gripping state.
Figure 12A:
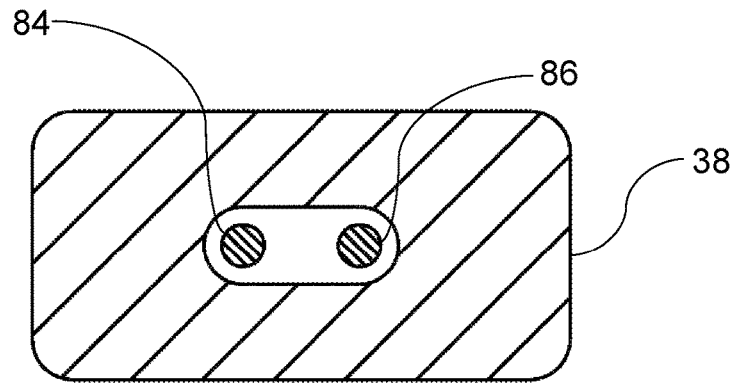
FIG. 12A is a transverse cross section of a deployment rod embodiment of FIG. 12 taken along lines 12A-12A of FIG. 12.

For some releasable anchor embodiments 31, each of the releasable anchors may have a shaft 70 with an elongate configuration having an axial length greater than an outer transverse dimension of the shaft 70. The releasable anchor 31 may be configured to be actuated between a curved tissue gripping state having the curved distal end 40 as shown in FIG. 12 and a straightened state as shown in FIG. 11. In some cases, the shaft 70 of the releasable anchor 31 may further include a sharpened distal end 72 which is configured to penetrate tissue such as the fascia tissue layer 3 when pushed distally, sharpened distal end 72 first, into the fascia tissue layer 3. For some embodiments, the shaft 70 may be made from or include an optional shape memory metal that can be actuated between the curved tissue gripping state shown in FIG. 16B and the straightened state shown in FIG. 11. For such embodiments, the shape memory metal of the shaft 70 may include nickel titanium alloy. For other such embodiments, the shaft 70 may include an optional a bi-metal structure that can be actuated between the curved tissue gripping state and the straightened state.

Figure 13:
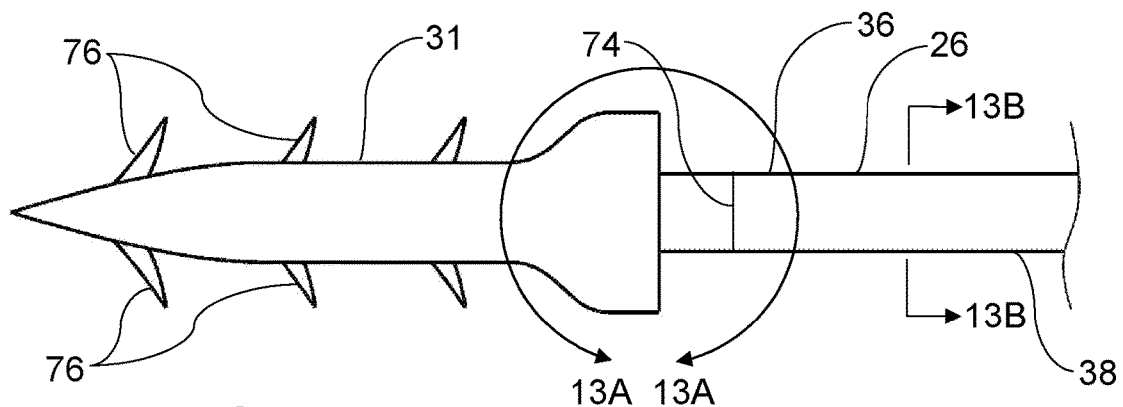
FIG. 13 is an elevation view of a detachable anchor embodiment.
Figure 13A:
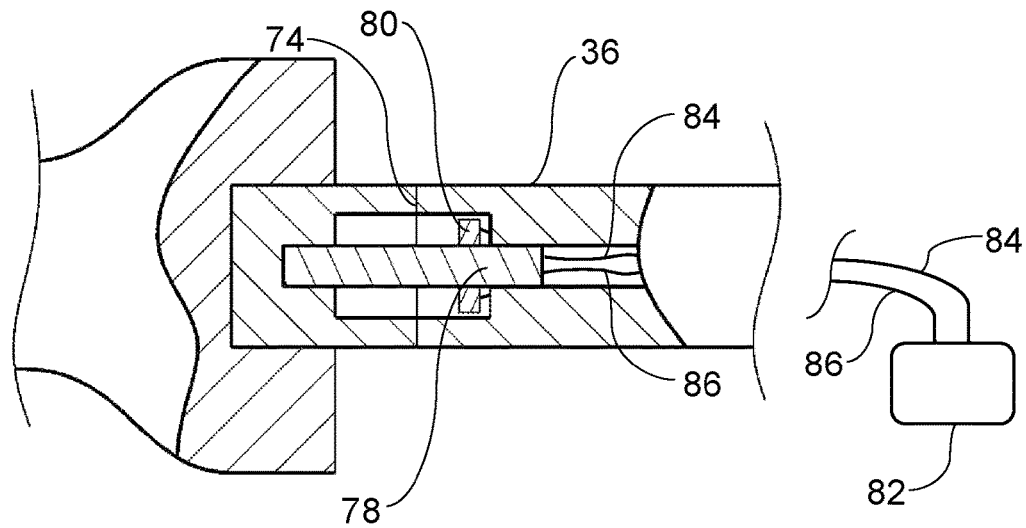
FIG. 13A is an enlarged view of the encircled portion 13A-13A of the detachable anchor embodiment of FIG. 13.
Figure 13B:
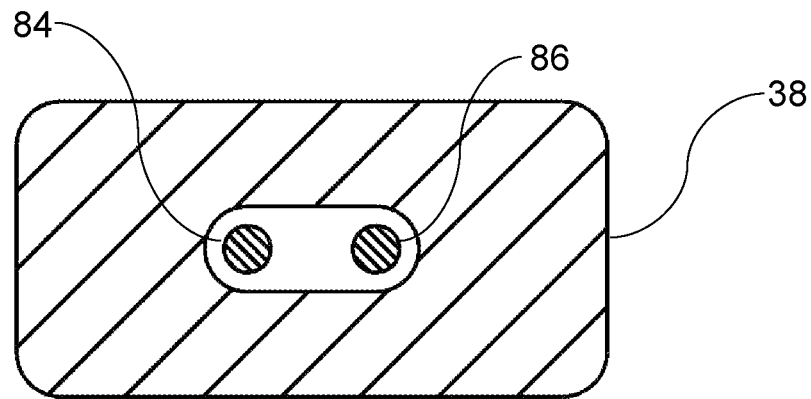
FIG. 13B is a transverse cross section of the deployment rod embodiment of FIG. 13 taken along lines 13B-13B of FIG. 13.
Figure 14:
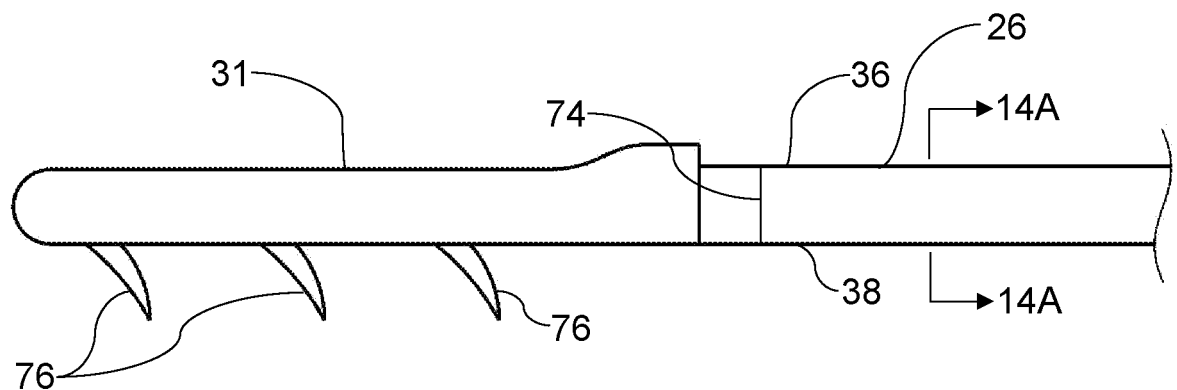
FIG. 14 is an elevation view of a detachable anchor embodiment.
Figure 14A:
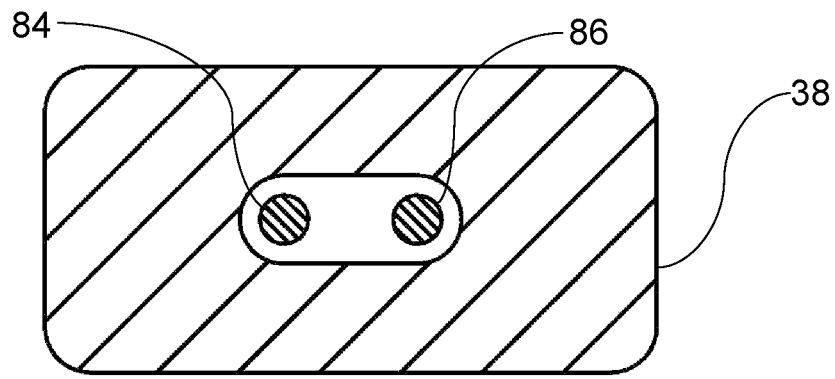
FIG. 14A is a transverse cross section of the deployment rod embodiment of FIG. 14 taken along lines 14A-14A of FIG. 14.
Figure 15:
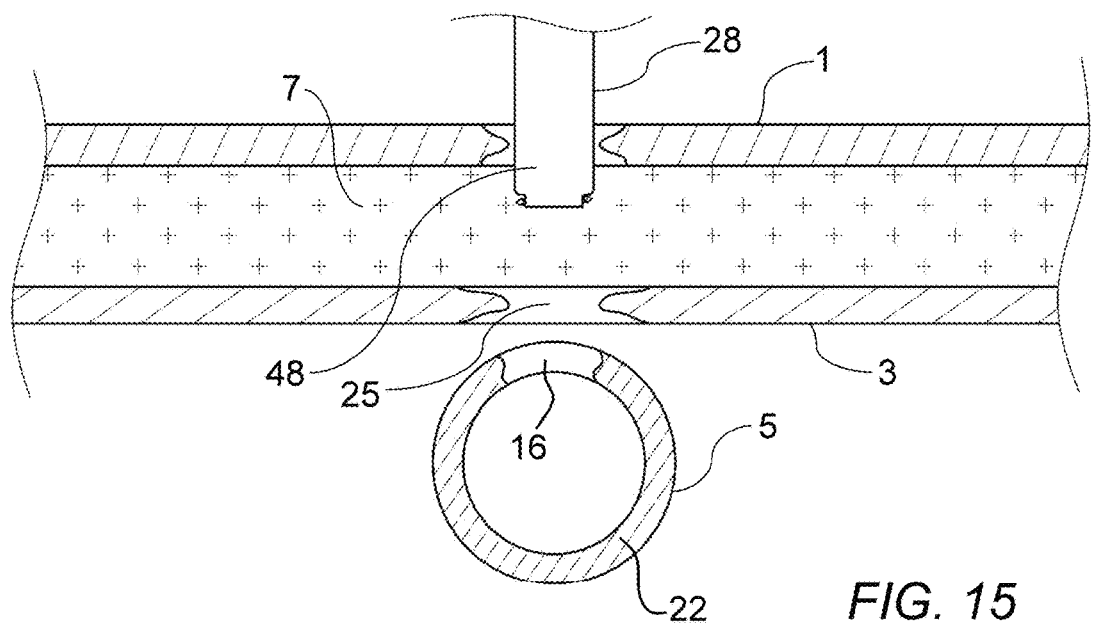
FIG. 15 is an elevation view in partial section of a distal section of a housing of a vascular closure device disposed adjacent an access hole of a fascia tissue layer.

In some cases, it may be desirable to use detachable anchors at the distal ends 36 of the deployment rods 38 and anchor deployers 26. Referring to FIGS. 13-14A, detachable anchor embodiments 31 are shown wherein the anchor deployers 26 include releasable junctions 74 disposed between each such detachable anchor 31 and respective deployment rod 38 which is secured thereto. In some cases, the detachable anchor embodiments 31 may include a proximally oriented barb 76, and in some cases, a plurality of proximally oriented barbs 76. For some embodiments, the releasable junctions 74 used to detach such detachable anchors 31 may include a releasable junction 74 released by thermal detachment, mechanical detachment or any other suitable detachment mechanism. The releasable junction embodiment 74 shown in FIG. 13A includes a tether 78 which secured between the distal end 36 of the deployment rod 38 and anchor 31 and which may be melted by a heater element 80 disposed about the tether 78. The heater element 80 may be actuated by applying electrical power from a power source 82 to the heater element 80 through a first electrically conducting wire 84 and a second electrically conducting wire 86 in electrical communication between the power source 82 and the heater element 80.

Some embodiments of the vascular closure devices discussed herein may include a lateral surface configured to extend radially from a distal extension of the housing 28 while the lateral surface is disposed within a blood vessel 5 such as the anvil 9 shown in FIG. 1 and the deployable positioning feature 20 shown in FIGS. 4A and 4B and discussed above. Such a lateral surface 9, 20 that extends radially may be used to provide a reference point between relative axial positions of the wall 22 of the blood vessel 5 and the anchors 31 prior to deployment of the anchors 31. In some cases, embodiments of the anchors 31 may be deployed a predetermined axial distance from the wall 22 of the blood vessel 5 as measured from the lateral surface 9, 20 which is disposed against the wall 22 of the blood vessel 5.

Figure 16:
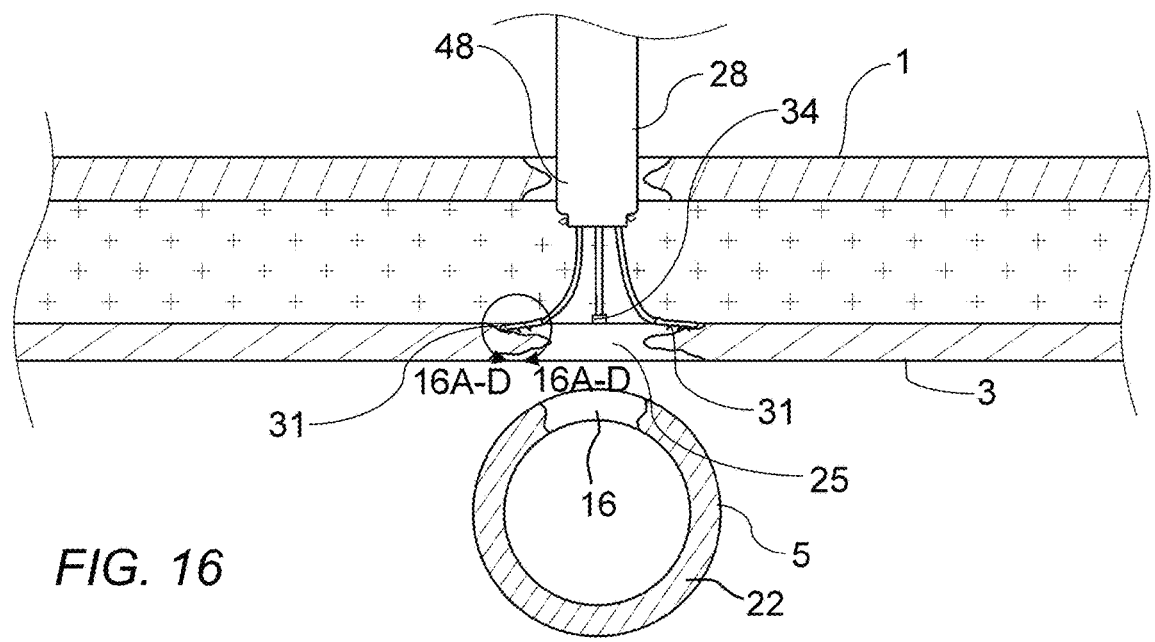
FIG. 16 shows the vascular closure device of FIG. 15 with the anchor deployers distally extended and with anchors thereof secured to the fascia tissue layer.
Figure 16A:
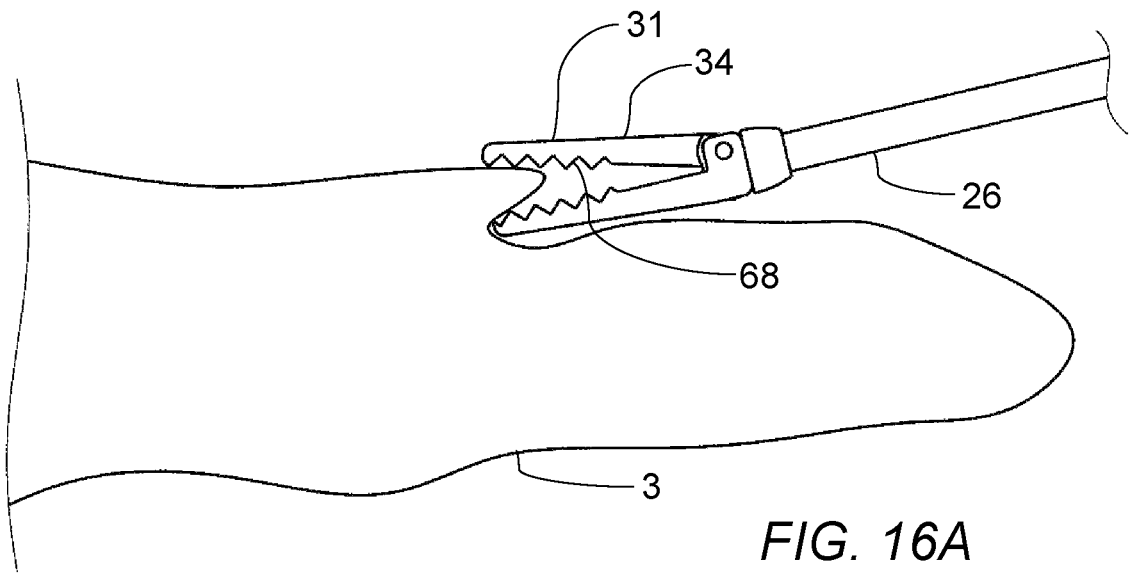
FIG. 16A shows the releasable anchor embodiment of FIG. 9 in a closed state and secured to fascia tissue.
Figure 16B:
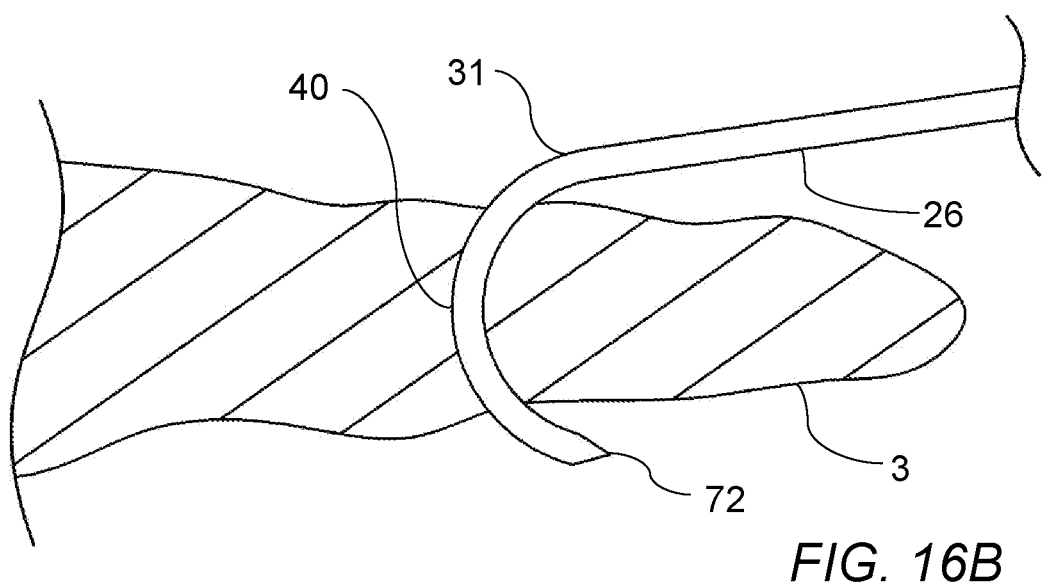
FIG. 16B shows the releasable anchor embodiment of FIG. 11 in a curved tissue gripping state secured to fascia tissue.

Referring generally to FIGS. 15-24, some embodiments of a method for vascular closure may include disposing the distal end 52 of the housing 28 of the vascular closure device 24 to a position adjacent the passage 25 in the tissue layer 3 and deploying a plurality of anchor deployers 26 from a distal section 48 of the housing 28. The anchor deployers 26 may be so deployed by distally advancing deployment rods 38 of the anchor deployers 26 in a distal and radially outward direction from the housing 28 into the tissue layer 3 in positions disposed about the passage 25 in the tissue layer 3. Respective anchors 31 of the anchor deployers 26 may then be secured to the tissue layer 3 in positions disposed about the passage 25 in the tissue layer 3 as shown in FIGS. 16A-16B. The deployment rods 38 may then be proximally retracted back into the distal section 48 of the housing 28 so as to draw the anchors 31 and respective tissue layer portions secured thereto together adjacent the distal section 48 of the housing 28 to gather the tissue 3 and close the passage 25 in the tissue layer 3. The deployment rods may be withdrawn with a spring or similar mechanism to apply a desired tension, or alternatively may be withdrawn with a lead screw, cam or similar mechanism to withdraw the deployment rods a desired distance independent of required tension. Thereafter, a tissue grip mechanism may be deployed over the anchors 31 and onto the tissue layer portions 32 gathered and secured to the anchors 31 so as to secure the tissue layer portions together with the access hole 25 closed or reduced. The anchors 31 may then be released from the tissue layer portions which are secured together as shown in FIGS. 20 and 21. Thereafter, the deployment rods 38 and anchors 31 of each of the plurality of anchor deployers 26 may be proximally withdrawn into the distal section 48 of the housing 28.

In some cases, for such method embodiments, it may be desirable after proximally retracting the anchors 31 and deployment rods 38 and gathering tissue of the tissue layer 3 and prior to deploying the tissue grip, to release the tissue layer 3 from the anchors 31 and re-deploy the anchor deployers 26 by re-extending the deployment rods 38 in a distal and radially outward direction and re-gripping the tissue layer 3 about the access passage 25 to reset the orientation and/or position of the anchors with respect to the access hole 25 before proximally retracting the anchors 31 and deployment rods 38 back into the housing 28. This may be particularly useful when the operator is not satisfied with the initial placement of the anchors 31 about the access hole 25 in the tissue layer 3. Such repositioning of the anchors 31 may be repeated as many times as is practical by the operator of the vascular closure device 24.

Figure 9:
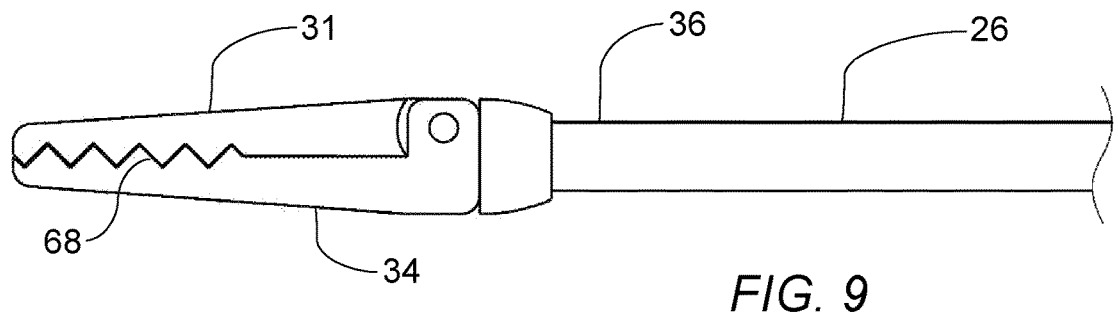
FIG. 9 is an elevation view of a releasable anchor embodiment in a closed state.
Figure 10:
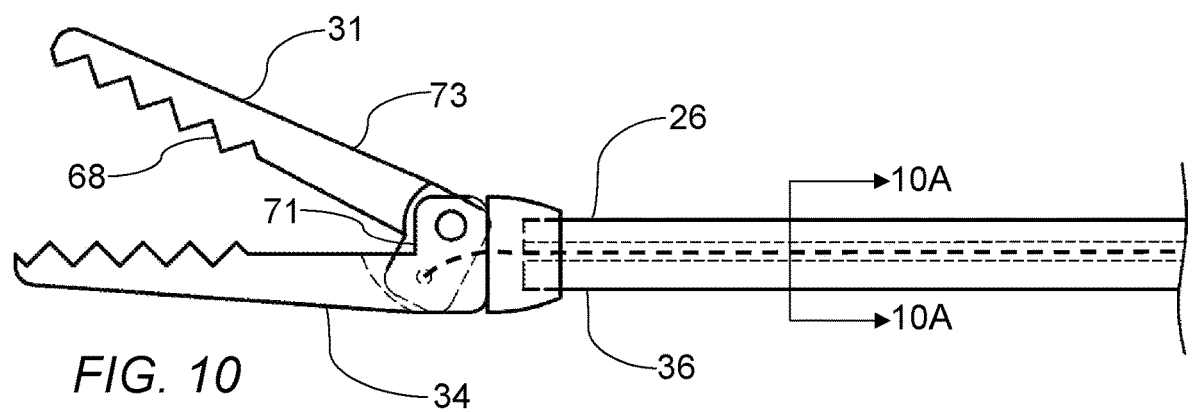
FIG. 10 is an elevation view of the releasable anchor embodiment of FIG. 9 in an open state.
Figure 10A:
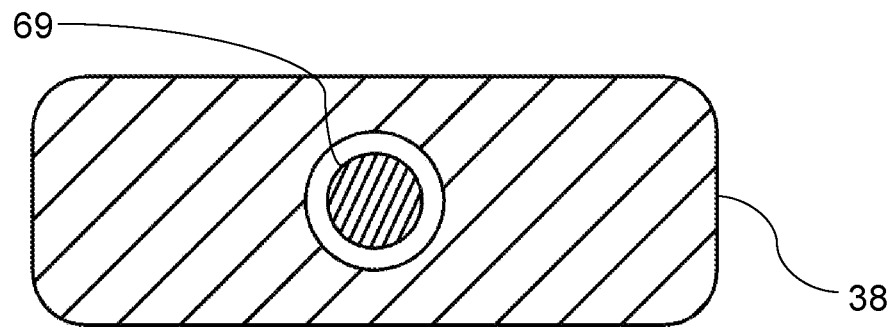
FIG. 10A is a transverse cross section of the deployment rod of FIG. 10 taken along lines 10A-10A of FIG. 10.

In some instances, the anchors 31 may include the jaws 34 that can be moved between an open state and a closed state as shown in FIGS. 9-10A. In such cases, securing the jaws 34 of the respective anchors 31 to the tissue layer 3 may include inserting tissue of the tissue layer 3 into the jaws 34 while the jaws 34 are in an open state and then closing the jaws 34 to the closed state to grip the tissue layer between the opposed surfaces of the jaws 34 as shown in FIG. 16A. In some cases, the jaws 34 may include the tissue gripping teeth 68 on the opposed surfaces of the jaws 34 and gripping the tissue 3 between the opposed surfaces of the jaws 34 may include engaging and partially penetrating the tissue layer with the tissue gripping teeth 68. In addition, for such embodiments, releasing the anchors 31 from the tissue layer portions may include moving the jaws 34 from the closed state to the open state such that the tissue is no longer gripped by the opposed surfaces of the jaws 34 or tissue gripping teeth 68 thereof.

For some embodiments of the vascular closure device 24, the anchors 31 may include the shaft 70 which has the sharpened distal end 72 and which has an elongate configuration with an axial length greater than an outer transverse dimension as shown in FIG. 11. The shaft 70 may be configured to be actuated between the curved tissue gripping state as shown in FIG. 12 and the straightened state as shown in FIG. 11. For such embodiments, securing such respective anchors 31 to the tissue layer 3 may include inserting the sharpened distal ends 72 of the shaft 70 into the tissue layer 3 with the shaft 70 in a straightened state and actuating the shaft 70 to move the shaft 70 into a curved tissue gripping state about tissue of the fascia tissue layer 3 as shown in FIG. 16B. For some such embodiments, releasing the anchors 31 from the tissue layer portions may include actuating the shafts 70 from the curved tissue gripping state to the straightened state and thereafter proximally retracting the shafts 70 from the tissue layer portions.

Figure 8A:
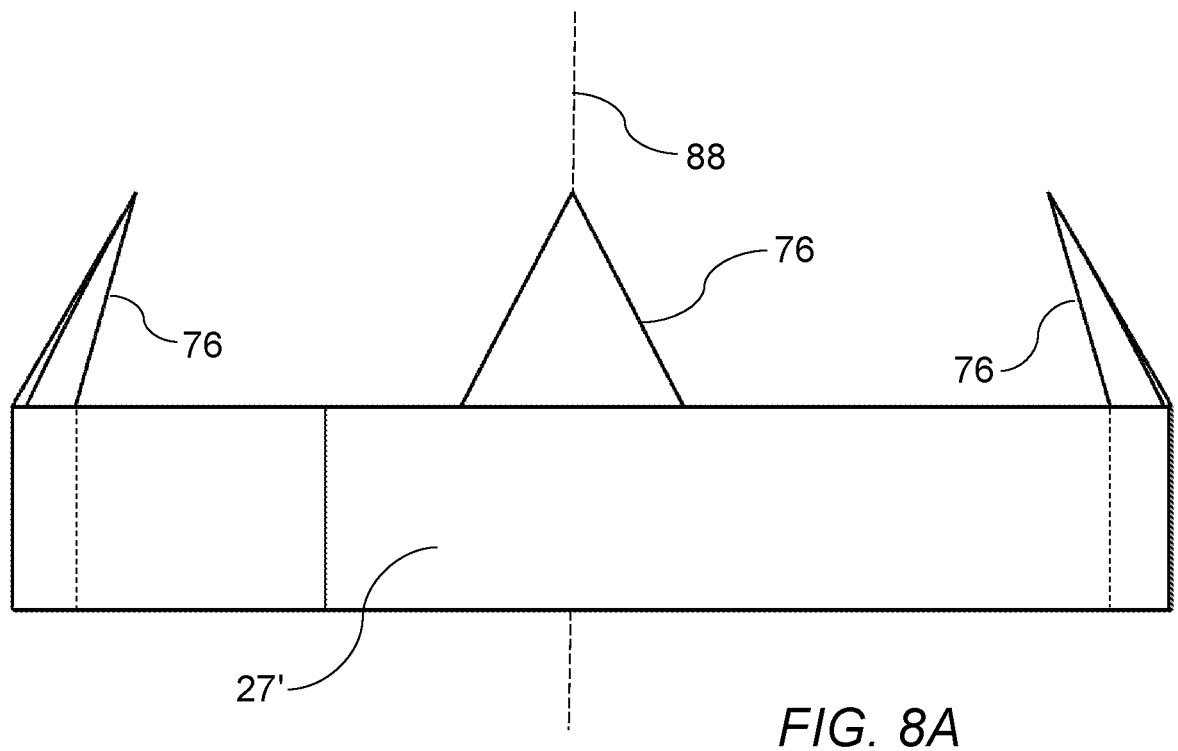
FIG. 8A is an elevation view of a lock ring embodiment.
Figure 8B:
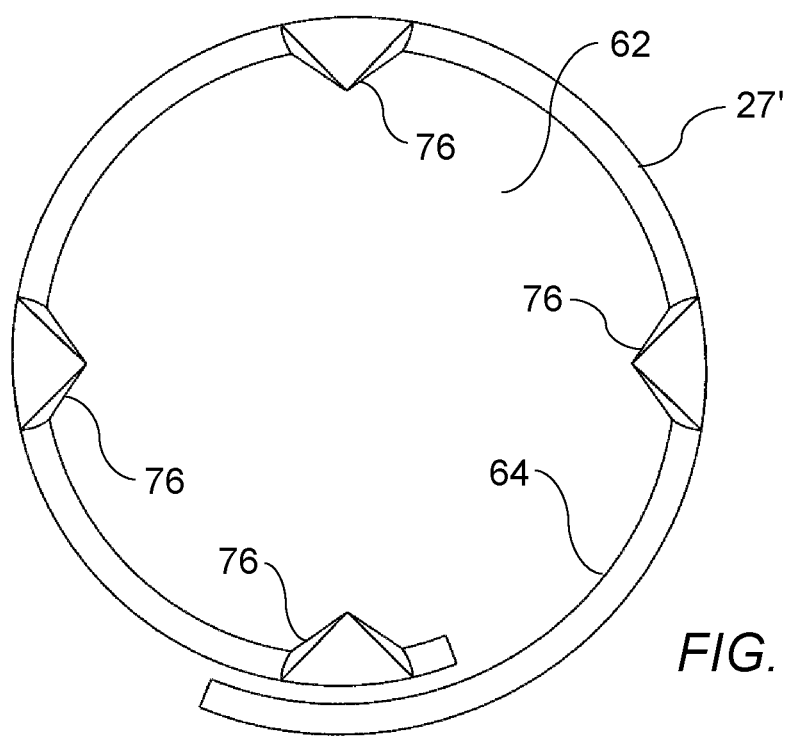
FIG. 8B is a top view of the lock ring embodiment of FIG. 8A.
Figure 8C:
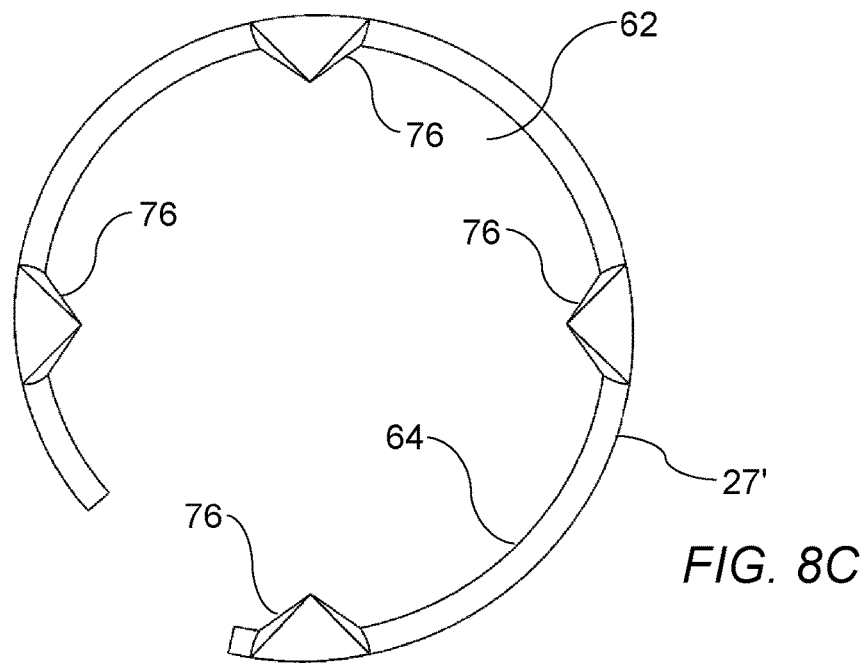
FIG. 8C is a top view of the lock ring embodiment of FIG. 8A in a radially expanded state.
Figure 22:
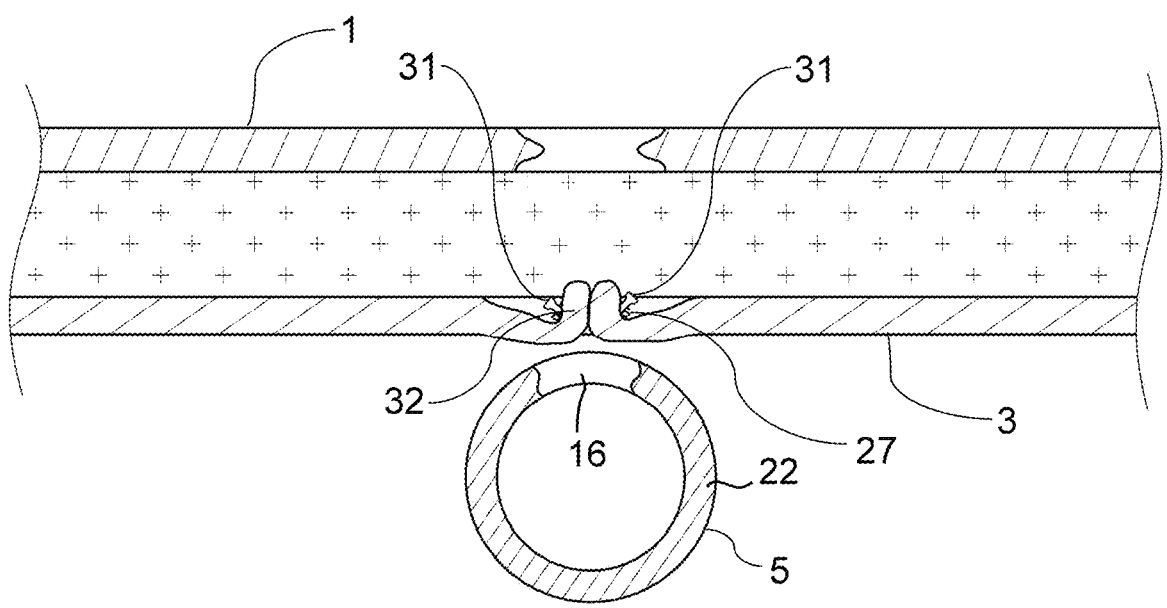
FIG. 22 shows portions of the fascia tissue layer disposed about the access hole in a gathered and secured state with the lock ring disposed thereon, the lock ring being further secured in fixed relation to the portions of fascia tissue by detachable anchors which are secured to the fascia tissue above the lock ring which may be mechanically captured by the deployed detachable tissue anchors.
Figure 23:
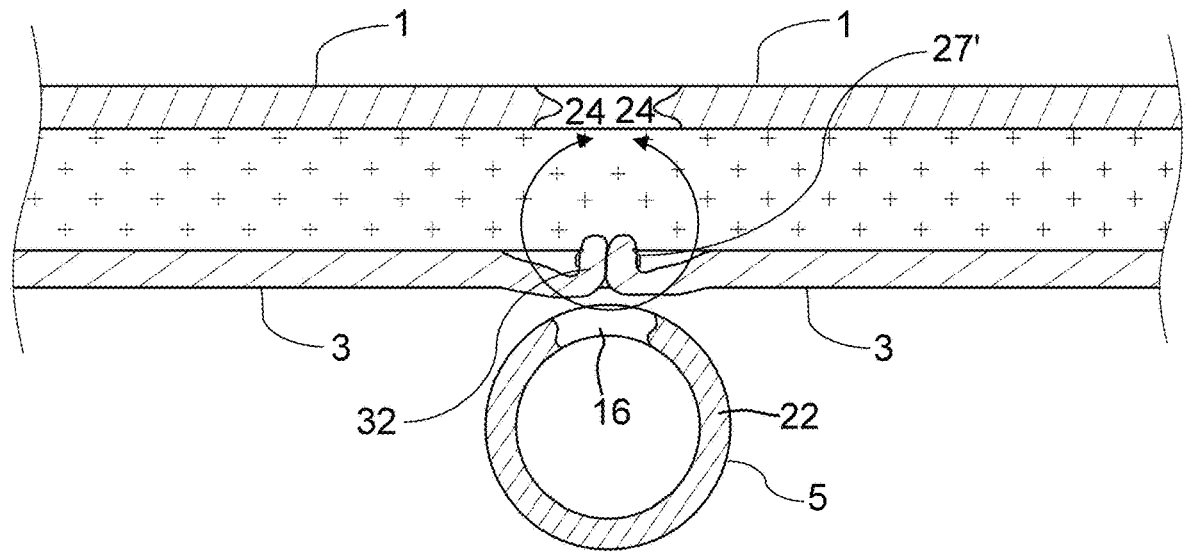
FIG. 23 shows a lock ring embodiment in a relaxed self-constrained state disposed about and securing portions of gathered fascia tissue layer.

In some instances, deploying the tissue grip mechanism onto the tissue layer portions may include sliding the self-contracting ring 27 in an expanded state from the distal end 52 of the housing 28 and allowing the self-contracting ring 27 to contract to the relaxed state over the tissue layer portions 3 as shown in FIGS. 20 and 22. The self-contracting ring 27 may optionally include a non-circular cross section, such as a diamond-shaped cross section, to increase friction with the tissue bundle 32. Such a self-contracting ring 27 may also include a self-contracting ring embodiment 27' that includes barbs 76 which point upward and radially inward towards a longitudinal axis 88 of the self-contracting ring 27' as shown in FIGS. 8A-8c. Once deployed over tissue 32 and allowed to self-contract to a relaxed constrained state, as shown in FIGS. 8A and 8B, the barbs 76 may penetrate into the gathered tissue 32 and prevent the lock ring 27' from sliding off of the gathered tissue 32 as shown in FIGS. 23 and 24. In some instances, deploying the tissue grip mechanism onto the gathered tissue 32 of the tissue layer portions 3 may include applying the tissue adhesive 30, such as cyanoacrylate to the gathered tissue 32 of the tissue layer portions as shown in FIGS. 20 and 21. FIG. 20 shows a tissue grip mechanism combination of the self-contracting ring 27 disposed over the gathered tissue 32 as well as the tissue adhesive 30 disposed thereon and in between different portions of the fascia tissue layer 3.

Figure 16C:
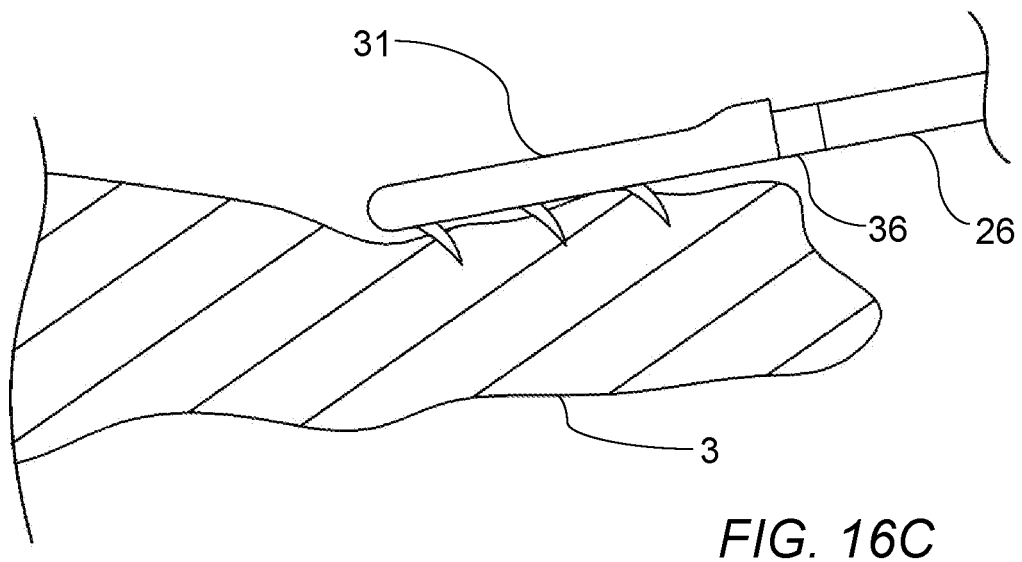
FIG. 16C shows the detachable anchor embodiment of FIG. 14 disposed in and secured to fascia tissue.
Figure 16D:
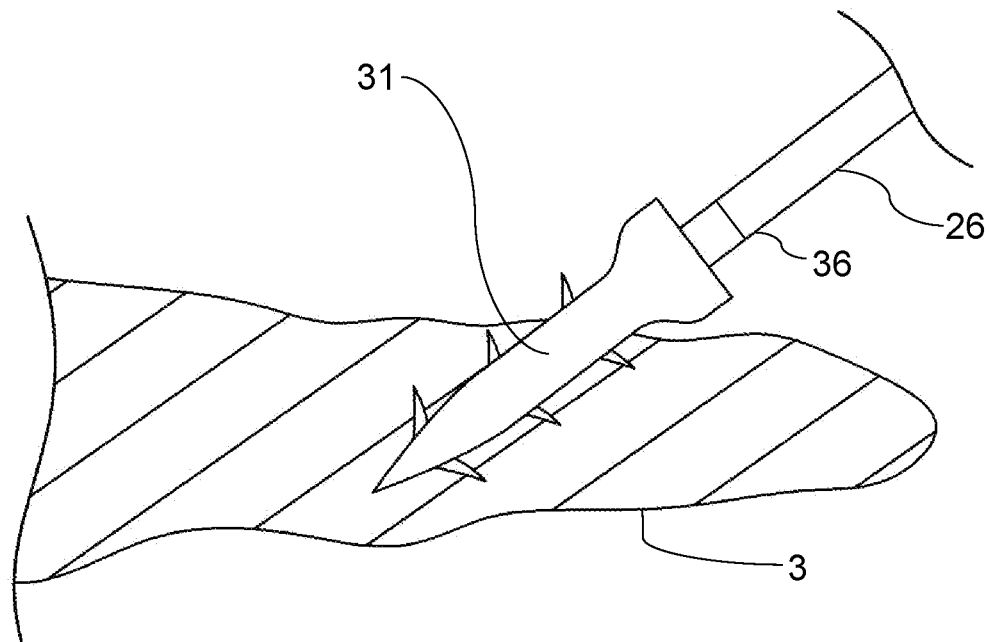
FIG. 16D shows the detachable anchor embodiment of FIG. 13 disposed in and secured to fascia tissue.
Figure 17:
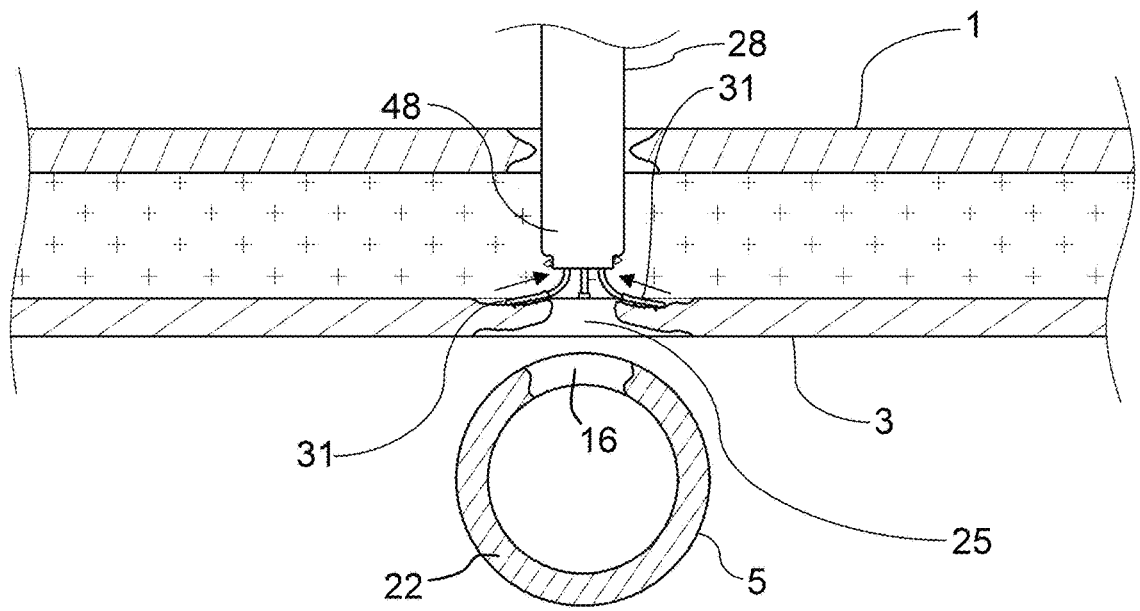
FIG. 17 shows the anchor deployers of the vascular closure device of FIG. 16 being proximally retracted and closing the access passage in the fascia tissue layer.
Figure 18:
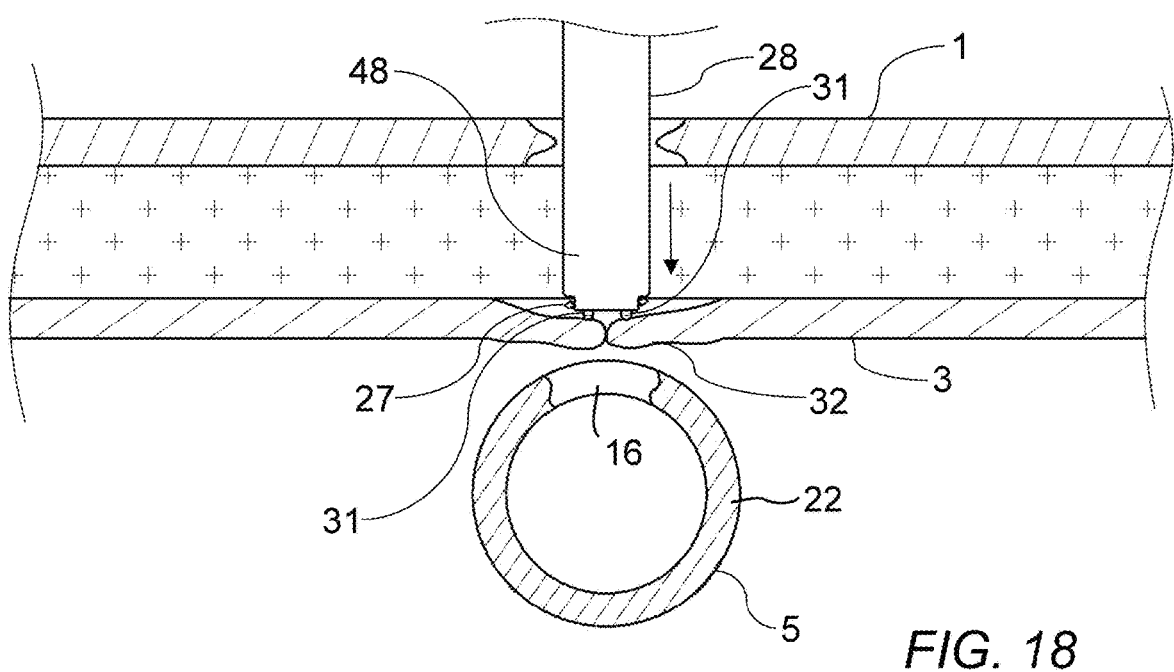
FIG. 18 is an elevation view in partial section showing the lock ring being deployed from the distal end of the housing of the vascular closure device of FIG. 5.
Figure 19:
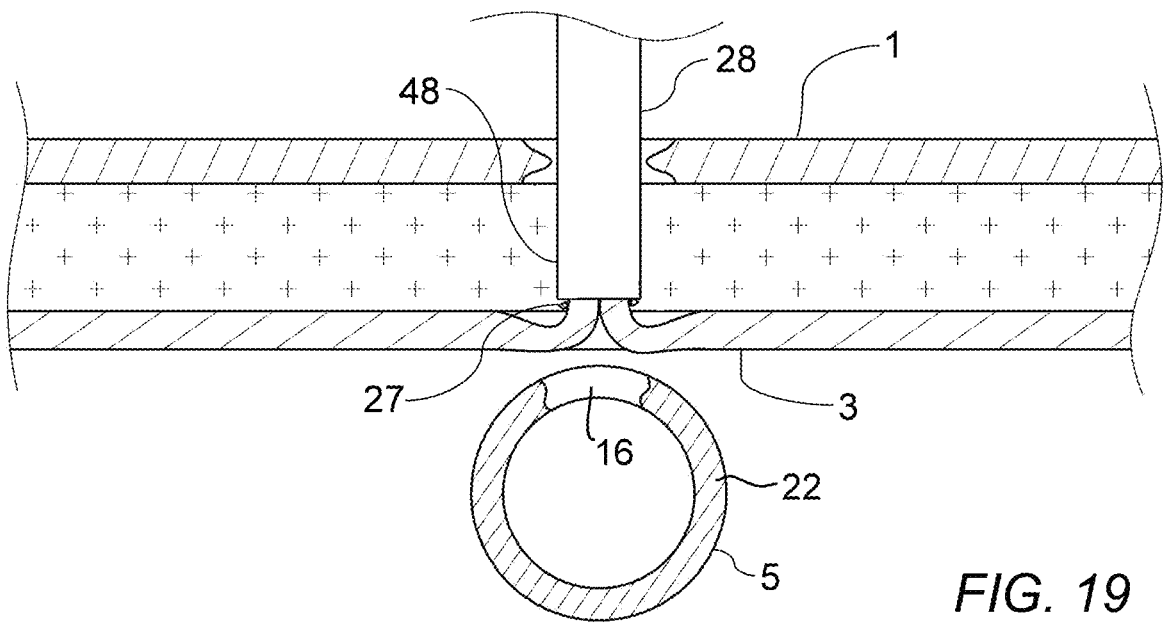
FIG. 19 shows the lock ring of FIG. 18 disposed around and securing portions of the fascia tissue layer gathered by the anchors of the vascular closure device of FIG. 5.

Referring again to FIGS. 15-24, some embodiments of a method for vascular closure may include disposing a distal end 52 of the housing 28 of the vascular closure device 24 to a position adjacent the access passage 25 in the tissue layer 3 and deploying a plurality of anchor deployers 26 from a distal section 52 of the housing 28. The anchor deployers 26 may be so deployed by distally advancing deployment rods 38 of the anchor deployers 26 in a distal and radially outward direction from the housing 28 into the tissue layer in positions disposed about the passage 25 in the tissue layer 3. Respective anchors 31 of the anchor deployers 26 may then be secured to the tissue layer 3 in positions disposed about the passage 25 in the tissue layer 3 as shown in FIGS. 16C-16D. The deployment rods 38 may then be proximally retracted back into the distal section 48 of the housing 28 so as to draw the anchors 31 and respective tissue layer portions secured thereto together adjacent the distal section 48 of the housing 28 to gather the tissue 3 and close the passage 25 in the tissue layer 3. Thereafter, the tissue grip embodiment may be deployed over the anchors 31 and onto the tissue layer portions 3 gathered and secured to the anchors 31 so as to secure the tissue layer portions together with the access hole 25 closed or reduced. The anchors 31 may then be detached from each of the respective deployment rods 38 secured thereto and left in the patient secured to the tissue layer 3. In some cases, the anchor deployers 26 may include the releasable junctions 74 disposed between each respective deployment rod 38 and anchor 31 thereof. In such cases, detaching each anchor 31 from the respective deployment rod 38 secured thereto may include heating a tether 78 of the releasable junction 74 until it melts. In some instances, the anchor deployers 26 may be mechanically attached to the anchors 31 via a quarter-turn lock. In such cases, a cam or similar mechanism in the handle 56 may be used to rotate each of the deployment rods 38 a quarter turn or other suitable angular displacement to disengage the deployment rods 38 from their respective anchors 31.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those

What is claimed is:

1. A method for vascular closure, comprising:
disposing a distal end of a housing of a vascular closure device to a position above and adjacent a passage in a tissue layer while the tissue layer is disposed above and adjacent an access hole in a wall of a blood vessel;
deploying a plurality of anchor deployers from a distal section of the housing by distally advancing deployment rods of the anchor deployers in a distal and radially outward direction from the housing into the tissue layer in positions disposed about the passage in the tissue layer;
securing respective anchors of the anchor deployers to the tissue layer in the positions disposed about the passage in the tissue layer;
proximally retracting the deployment rods back into the distal section of the housing so as to draw the anchors and respective tissue layer portions secured thereto together adjacent the distal section of the housing thereby closing the passage in the tissue layer and achieving a tissue lock indirectly sealing the access hole in the blood vessel while the tissue layer is disposed above and adjacent the access hole in the wall of the blood vessel;
deploying a tissue grip over the anchors and onto the tissue layer portions secured to the anchors so as to secure the tissue layer portions together; and
actuating the anchors to release them from the tissue layer portions prior to withdrawal of the anchors into the distal section of the housing.

2. The method of claim 1 further comprising releasing the anchors from the tissue layer portions prior to deploying the tissue grip and re-deploying the plurality of anchor deployers from the distal section of the housing by distally advancing the deployment rods of the anchor deployers in the distal and radially outward direction from the housing into the tissue layer in the positions disposed about the passage in the tissue layer, re-securing the respective anchors of the anchor deployers to the tissue layer in the positions disposed about the passage in the tissue layer; and proximally retracting the deployment rods back into the distal section of the housing a second time so as to draw the anchors and respective tissue layer portions secured thereto together adjacent the distal section of the housing.

3. The method of claim 1 wherein the anchors comprise jaws that can be moved between an open state and a closed state, wherein securing the respective anchors to the tissue layer comprises inserting tissue of the tissue layer into the jaws while in the open state and then closing the jaws to the closed state to grip the tissue layer.

4. The method of claim 3 wherein releasing the anchors from the tissue layer portions comprises moving the jaws from the closed state to the open state.

5. The method of claim 1 wherein each of the anchors comprise a shaft including a sharpened distal end and having an elongate configuration with an axial length greater than an outer transverse dimension, the shafts being configured to be actuated between a curved tissue gripping state and a straightened state, and wherein securing the respective anchors to the tissue layer comprises inserting the sharpened distal ends of the shafts into the tissue layer with the shafts in the straightened state and actuating the shafts to move the shafts into the curved tissue gripping state.

6. The method of claim 5 wherein releasing the anchors from the tissue layer portions comprises actuating the shafts from the curved tissue gripping state to the straightened state and proximally retracting the shafts from the tissue layer portions.

7. The method of claim 1 further comprising proximally withdrawing the deployment rods and the anchors of each of the plurality of anchor deployers into the distal section of the housing.

8. The method of claim 1 wherein deploying the tissue grip onto the tissue layer portions comprises sliding a self-contracting ring in an expanded state from the distal end of the housing and allowing the self-contracting ring to contract to a relaxed state over the tissue layer portions.

9. The method of claim 1 wherein deploying the tissue grip onto the tissue layer portions comprises applying a tissue adhesive to the tissue layer portions.

10. The method of claim 9 wherein applying the tissue adhesive to the tissue layer portions comprises applying cyanoacrylate adhesive to the tissue layer portions.

11. A method for vascular closure, comprising:
disposing a distal end of a housing of a vascular closure device to a position above and adjacent a passage in a tissue layer while the tissue layer is disposed above and adjacent an access hole in a wall of a blood vessel;
deploying a plurality of anchor deployers from a distal section of the housing by distally advancing deployment rods of the anchor deployers in a distal and radially outward direction from the housing into the tissue layer in positions disposed about the passage in the tissue layer;
securing respective anchors of the anchor deployers to the tissue layer in the positions disposed about the passage in the tissue layer;
proximally retracting the deployment rods back into the distal section of the housing so as to draw the anchors and respective tissue layer portions secured thereto together adjacent the distal section of the housing thereby closing the passage in the tissue layer and achieving a tissue lock indirectly sealing the access hole in the blood vessel while the tissue layer is disposed above and adjacent the access hole in the wall of the blood vessel;
deploying a tissue grip over the anchors and onto the tissue layer portions secured to the anchors so as to secure the tissue layer portions together; and
detaching each anchor from the respective deployment rod secured thereto.

12. The method of claim 11 wherein the anchor deployers comprise releasable junctions disposed between each respective deployment rod and anchor thereof, and wherein detaching each anchor from the respective deployment rod secured thereto comprises heating a tether of the releasable junction until the releasable junction melts.

13. A method for vascular closure, comprising:
disposing a vascular closure device adjacent a passage in a tissue layer while the tissue layer is disposed above and adjacent an access hole in a wall of a blood vessel of a patient;

deploying a plurality of anchors from a distal section of the vascular closure device in a distal and radially outward direction therefrom and engaging the tissue layer in positions disposed about the passage in the tissue layer with the anchors while the tissue layer is disposed above and adjacent the access hole in the wall of the blood vessel;

securing the anchors to the tissue layer in the positions disposed about the passage in the tissue layer;

proximally retracting the anchors closer together so as to draw the anchors and respective tissue layer portions secured thereto together thereby closing the passage in the tissue layer and achieving a tissue lock indirectly sealing the access hole in the blood vessel while the tissue layer is disposed above and adjacent the access hole in the wall of the blood vessel; and deploying a tissue grip onto the tissue layer portions drawn together by the anchors so as to secure the drawn together tissue layer portions.

14. The method of claim 13 wherein deploying the tissue grip onto the tissue layer portions drawn together by the anchors comprises deploying a lock ring onto the drawn together tissue layer portions.

15. The method of claim 13 wherein deploying the tissue grip onto the tissue layer portions drawn together by the anchors comprises deploying a tissue adhesive onto the drawn together tissue layer portions.

16. The method of claim 13 wherein the tissue layer comprises a facia layer, and wherein disposing the vascular closure device adjacent the passage in the tissue layer while the tissue layer is disposed above and adjacent the access hole in the wall of the blood vessel comprises disposing the vascular closure device adjacent the passage in the fascia layer while the fascia layer is disposed above and adjacent the access hole in the wall of the blood vessel.

* * * * *